(12) United States Patent
Godara et al.

(10) Patent No.: US 10,034,762 B2
(45) Date of Patent: Jul. 31, 2018

(54) DEVICES AND METHODS FOR TREATING TISSUE DEFECTS

(71) Applicant: Anchor Orthopedics XT Inc., Mississauga (CA)

(72) Inventors: Neil Godara, Milton (CA); Youssef Biadillah, Lausanne (CH)

( * ) Notice: Subject to any disclaimer, the term of this patent is extended or adjusted under 35 U.S.C. 154(b) by 377 days.

(21) Appl. No.: 14/727,141

(22) Filed: Jun. 1, 2015

(65) Prior Publication Data

US 2015/0335447 A1  Nov. 26, 2015

Related U.S. Application Data

(62) Division of application No. 13/509,410, filed as application No. PCT/CA2010/001762 on Nov. 12, 2010, now Pat. No. 9,078,761.

(60) Provisional application No. 61/260,845, filed on Nov. 12, 2009.

(51) Int. Cl.
*A61F 2/46* (2006.01)
*A61F 2/44* (2006.01)
*A61F 2/30* (2006.01)

(52) U.S. Cl.
CPC ............ *A61F 2/442* (2013.01); *A61F 2/4611* (2013.01); *A61F 2/441* (2013.01); *A61F 2002/3055* (2013.01); *A61F 2002/30299* (2013.01); *A61F 2002/30484* (2013.01); *A61F 2002/30545* (2013.01); *A61F 2002/30579* (2013.01); *A61F 2002/444* (2013.01); *A61F 2002/4435* (2013.01)

(58) Field of Classification Search
CPC .... A61F 2/44; A61F 2/442; A61F 2/46; A61F 2/4611
See application file for complete search history.

(56) References Cited

U.S. PATENT DOCUMENTS

| 6,425,919 B1 * | 7/2002 | Lambrecht | A61B 5/1076 623/17.16 |
| 2007/0100348 A1 * | 5/2007 | Cauthen, III | A61B 17/0401 606/99 |
| 2008/0065218 A1 * | 3/2008 | O'Neil | A61F 2/442 623/17.16 |
| 2011/0153022 A1 * | 6/2011 | Singhatat | A61F 2/441 623/17.16 |

* cited by examiner

*Primary Examiner* — Christopher Beccia
(74) *Attorney, Agent, or Firm* — Nir Lifshitz; Glenn Arnold

(57) ABSTRACT

The present disclosure describes embodiments for treating a defect in a tissue, the tissue having internal and external surfaces. A device includes a first portion for positioning at one of the internal and external surfaces for applying a treatment force to the defect. In addition, the device has a second portion for applying a counter-force, where the second portion is operable to be positioned so that the counter-force is applied on the other of the internal and external surfaces, away from the defect so as to substantially avoid application of force at the defect. Furthermore, the device includes a coupling member for connecting the inner and outer portions. Methods of using the device are described, for example in an intervertebral disc having a herniation.

23 Claims, 26 Drawing Sheets

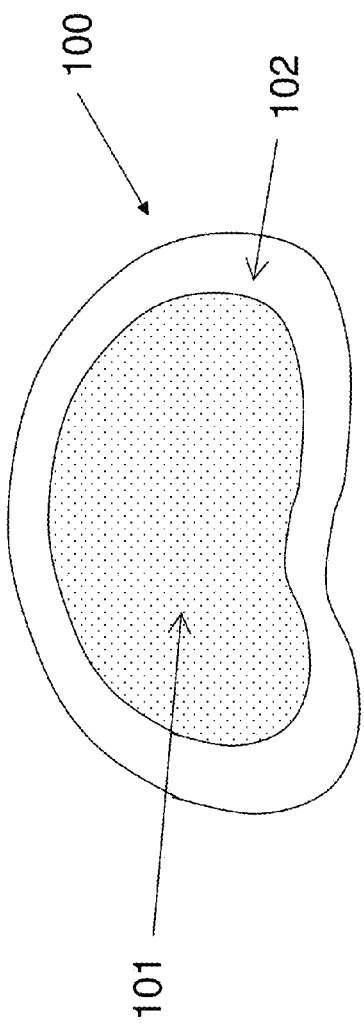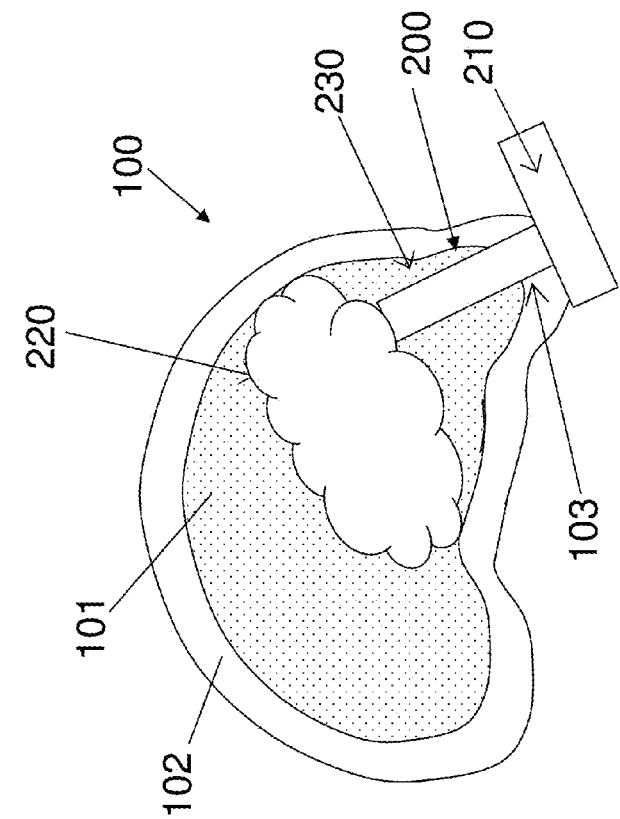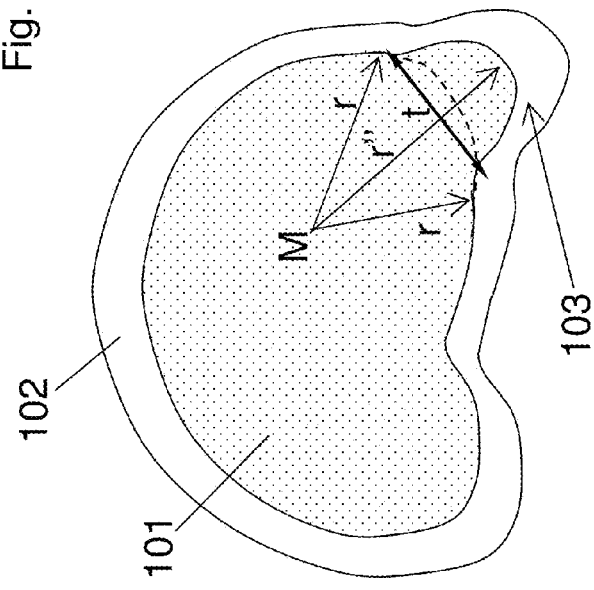

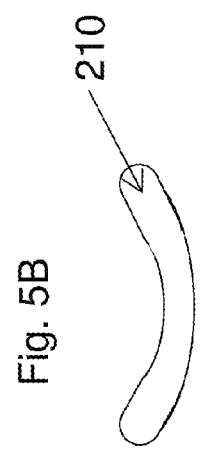
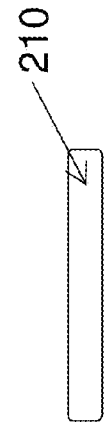
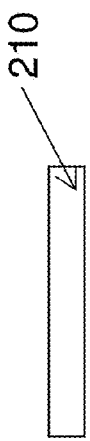
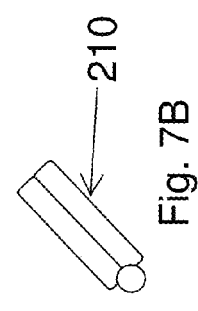
Fig. 4B   Fig. 5B   Fig. 6B   Fig. 7B
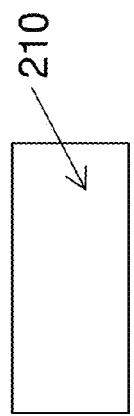
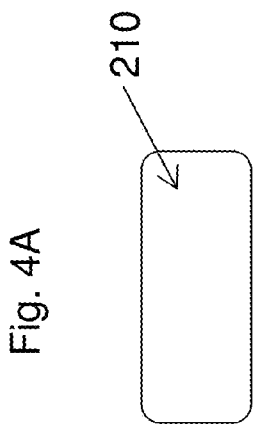
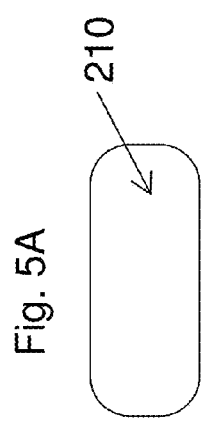
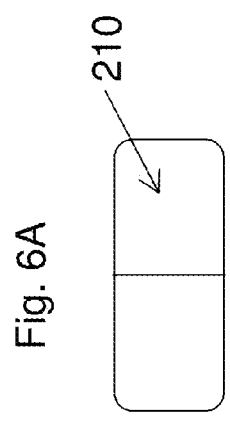
Fig. 4A   Fig. 5A   Fig. 6A   Fig. 7A

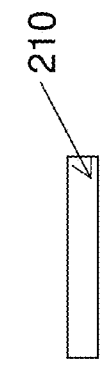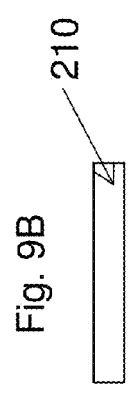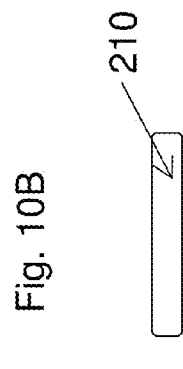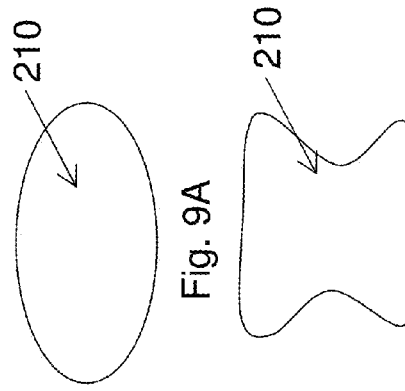

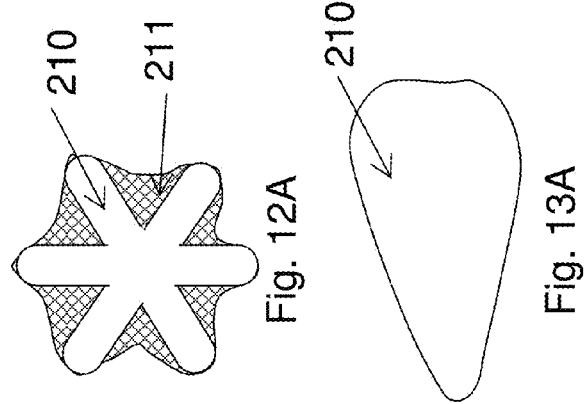
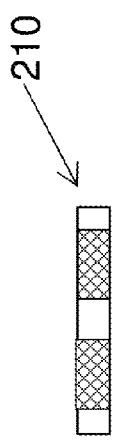
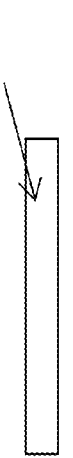
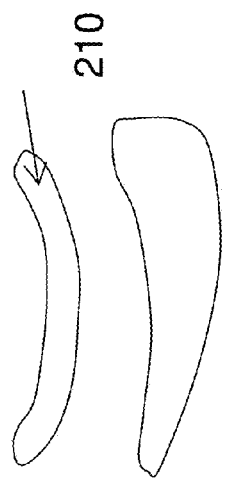
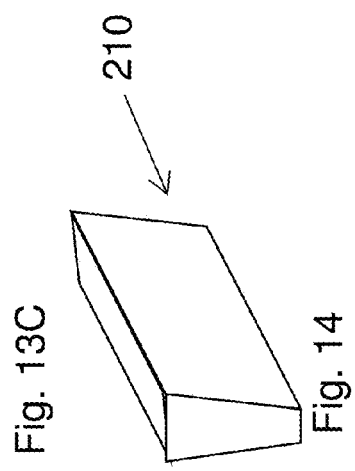
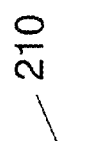

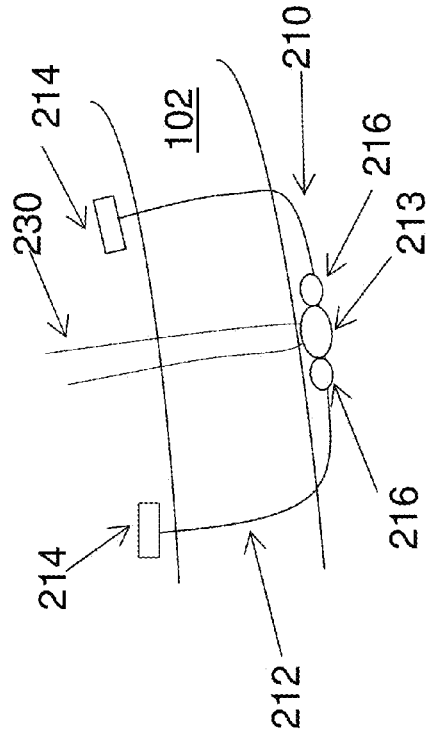
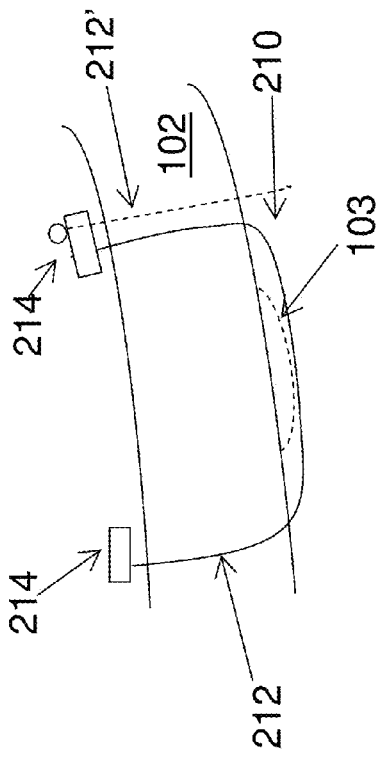
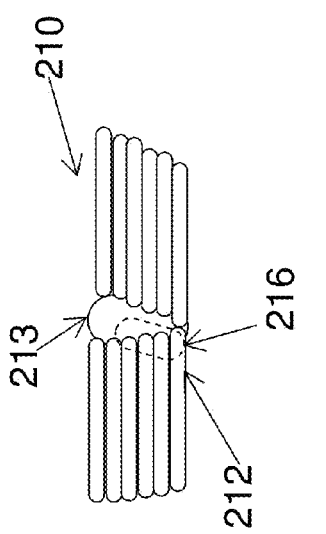
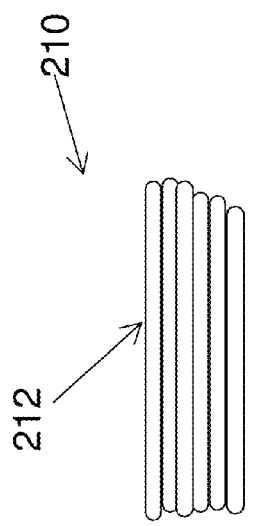

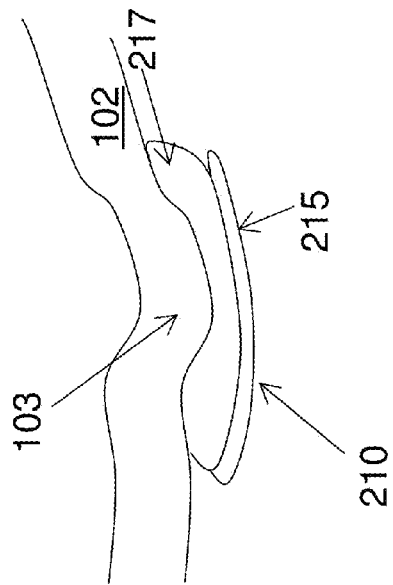
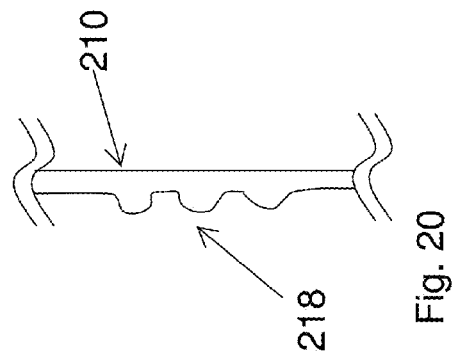
Fig. 18B
Fig. 20
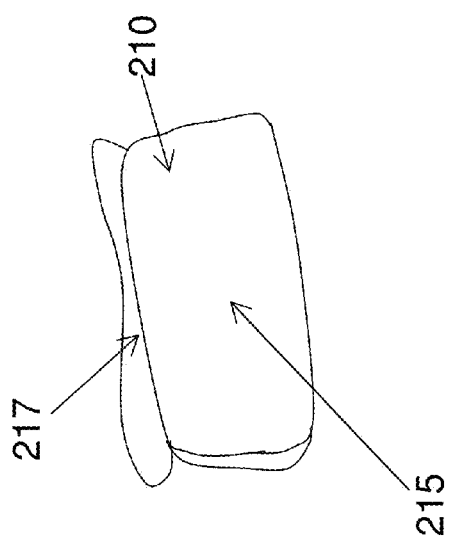
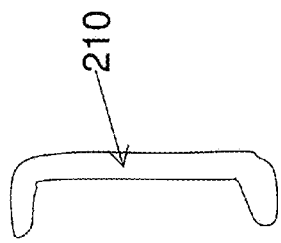
Fig. 18A
Fig. 19

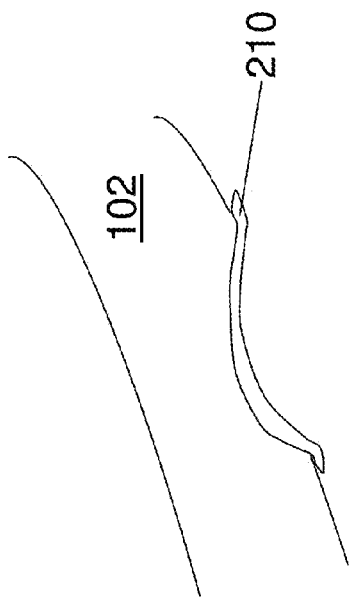
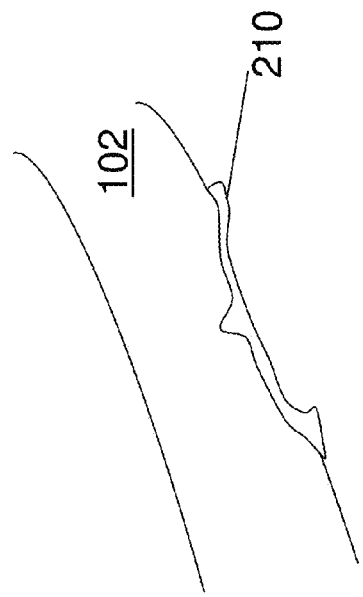
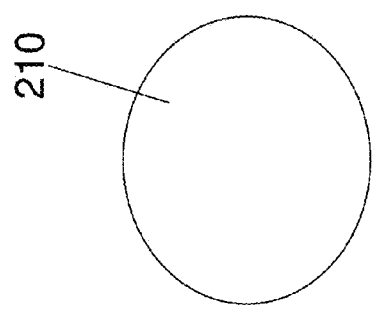
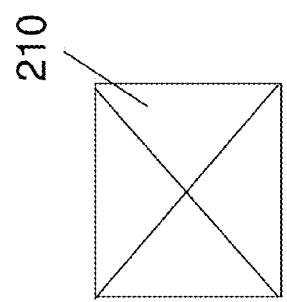
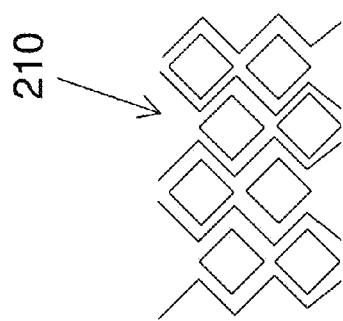
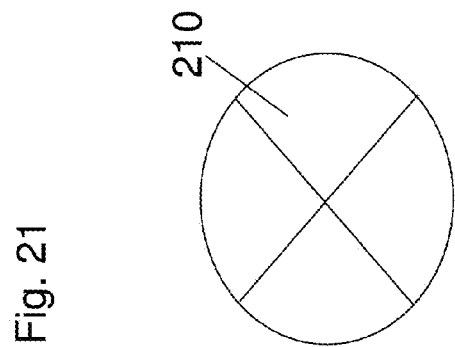

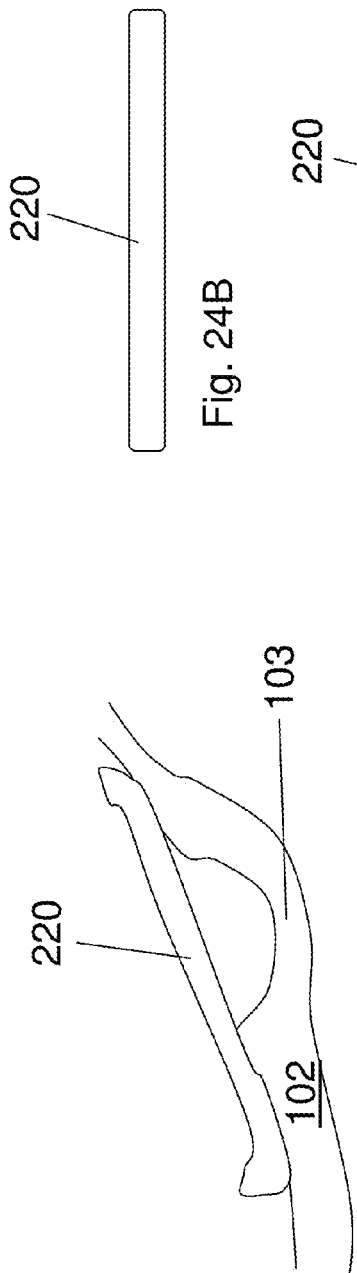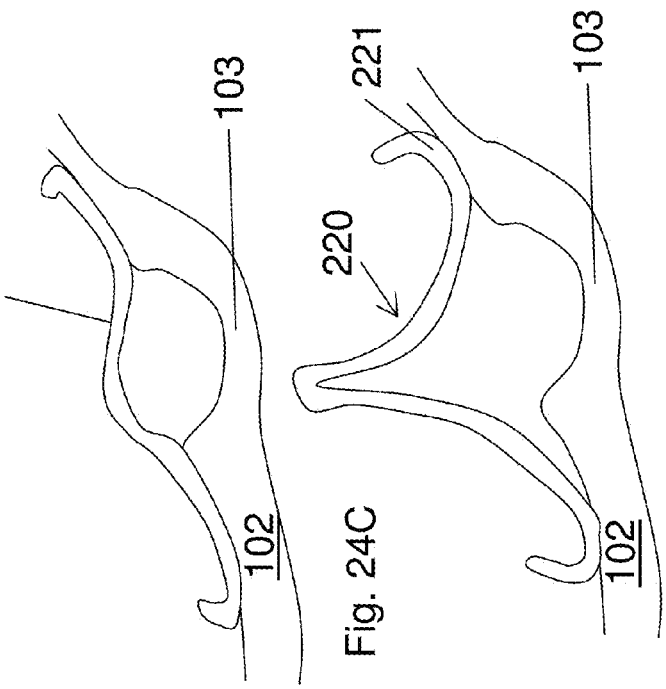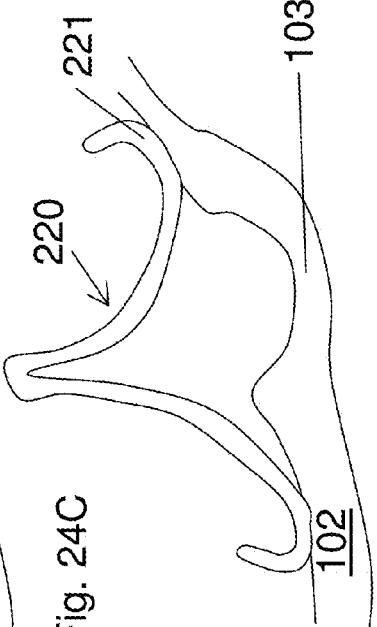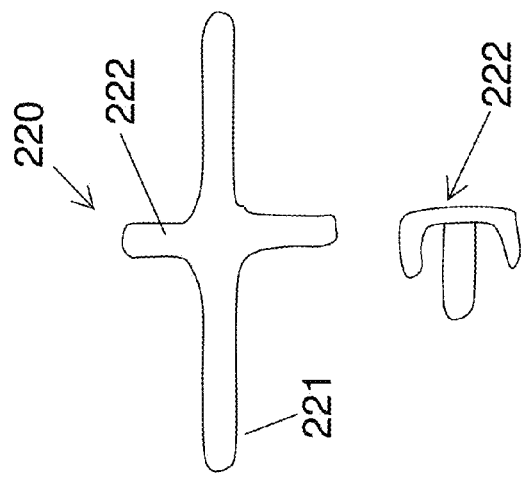
Fig. 24A, Fig. 24B, Fig. 24C, Fig. 24D, Fig. 24E

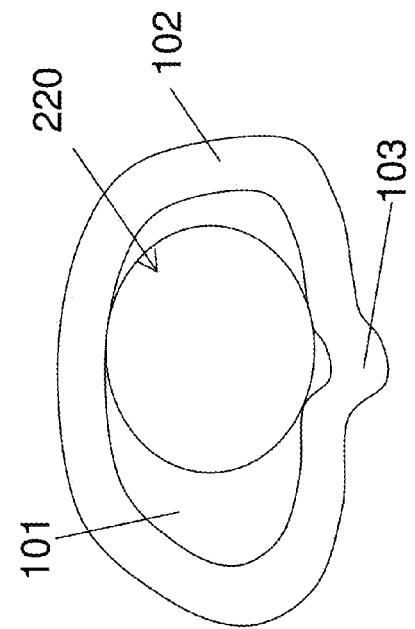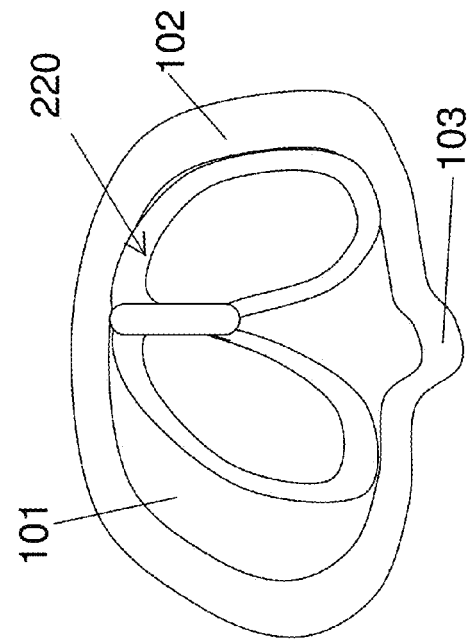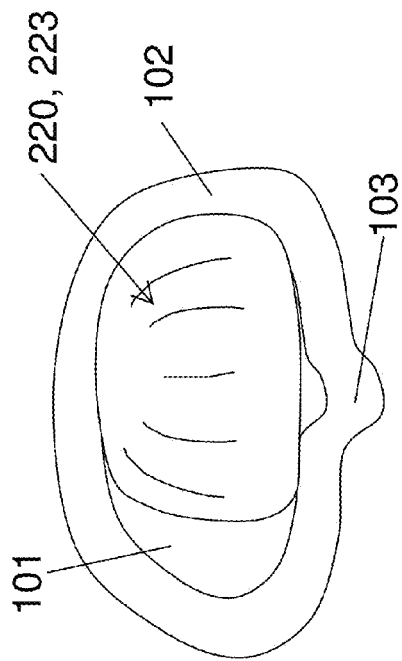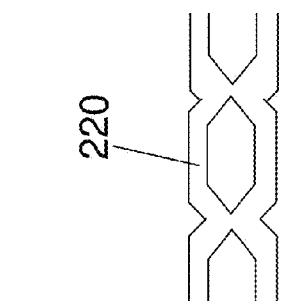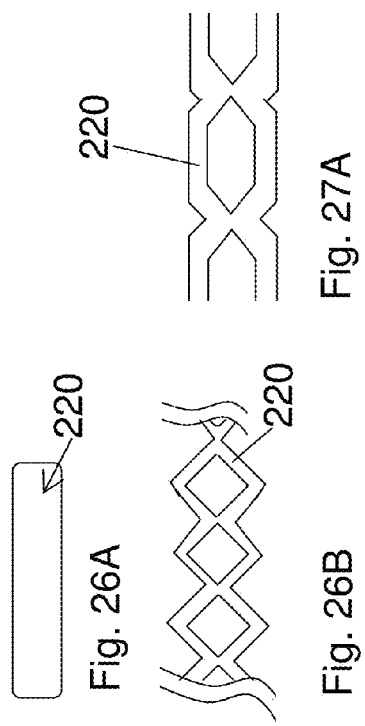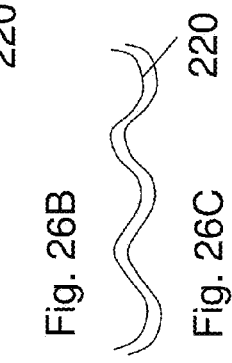

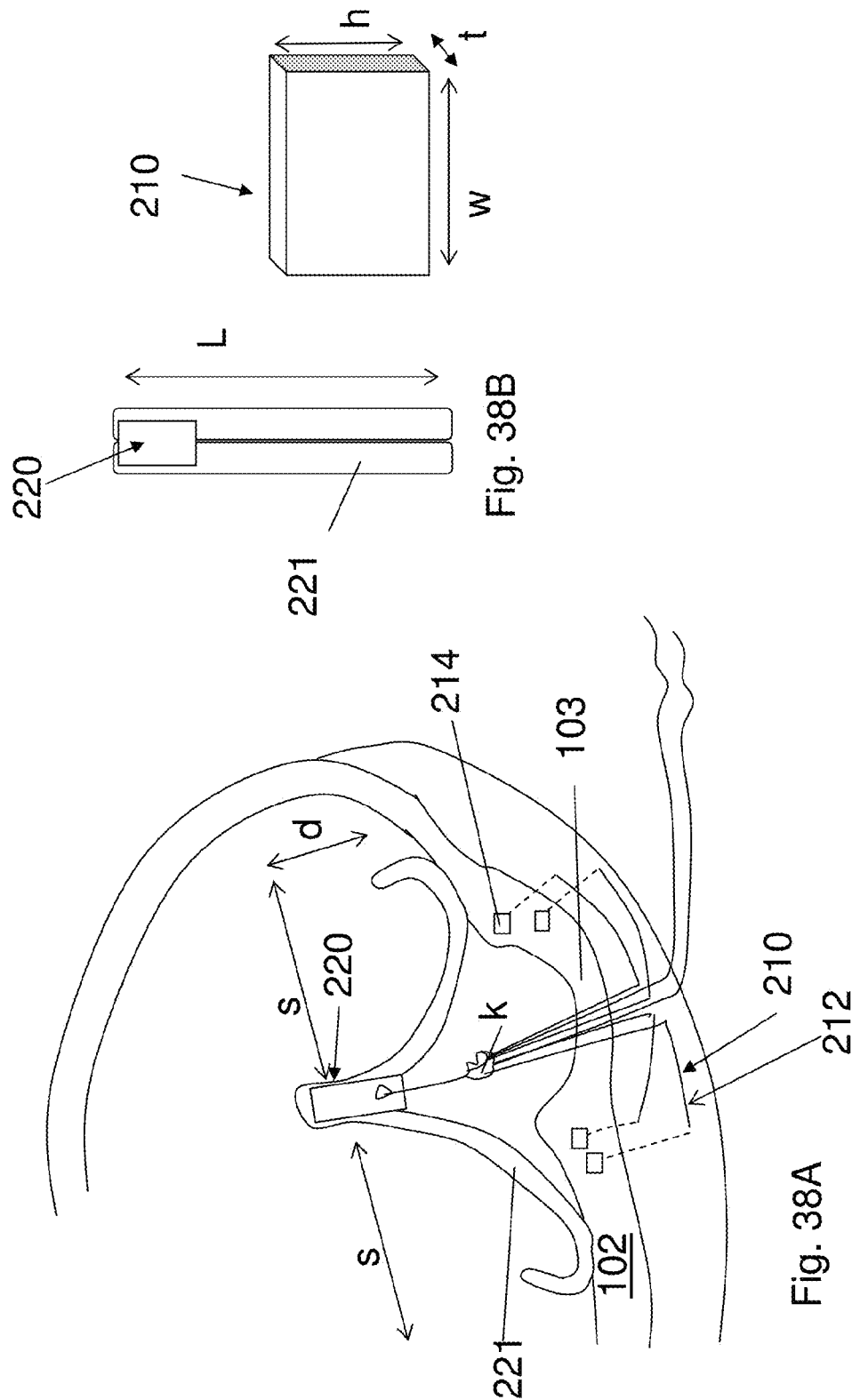

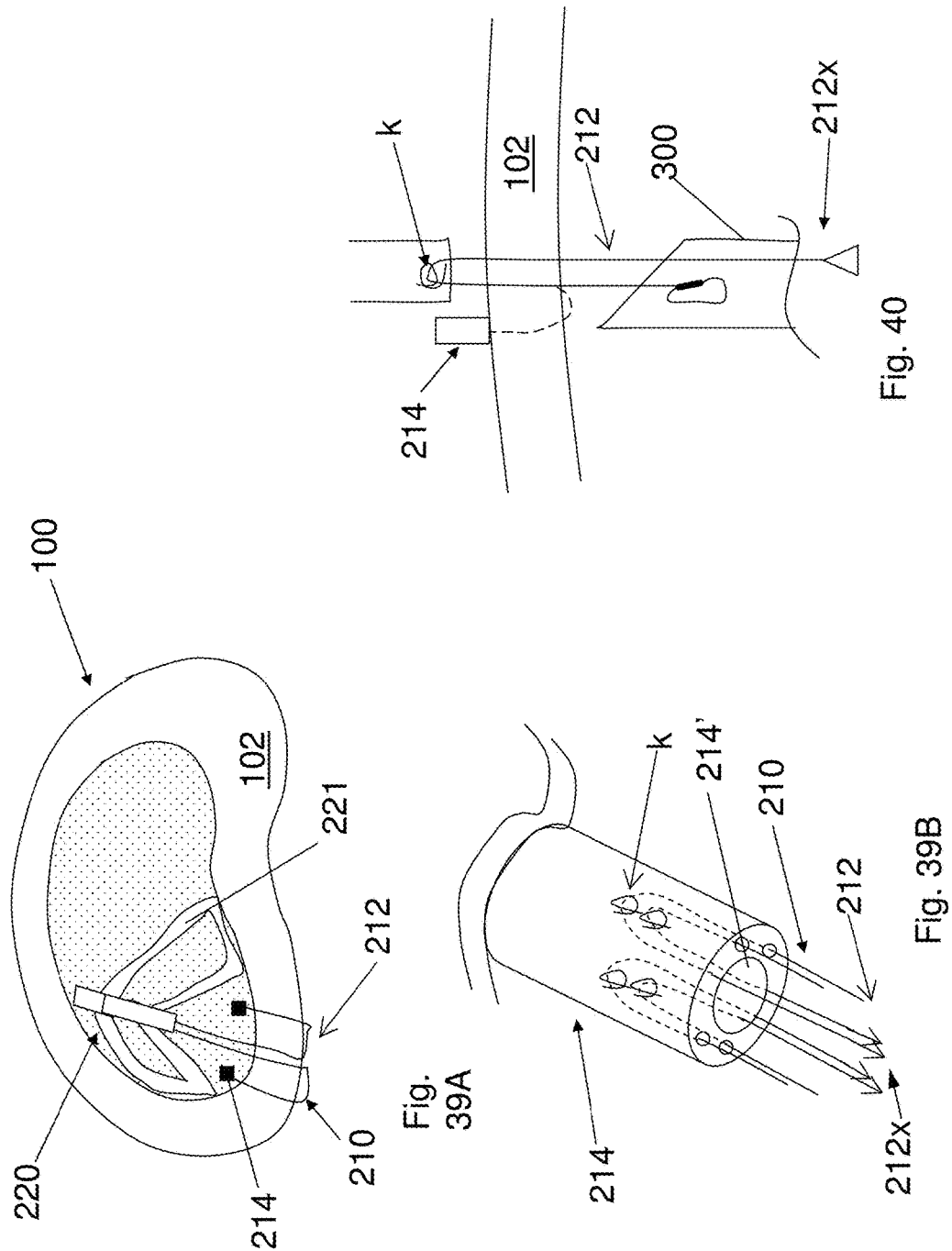

DEVICES AND METHODS FOR TREATING TISSUE DEFECTS

REFERENCES TO OTHER APPLICATIONS

This application claims the benefit of U.S. Provisional Patent Application Ser. No. 61/260,845, filed on Nov. 12, 2009 hereby incorporated by reference in its entirety.

TECHNICAL FIELD

The disclosure relates to devices and methods used to treat a defect within a region of tissue within a patient's body. More specifically, the disclosure relates to devices and methods used for treating a defect within an intervertebral disc.

SUMMARY OF THE DISCLOSURE

The present disclosure describes embodiments for treating a defect in a region of tissue by applying a force at a surface of the tissue containing the defect to treat the defect while a counter-force is applied away from the region of tissue containing the defect, such that the counter-force is substantially not applied at the region of tissue containing the defect.

To that end, a device for treating a defect within a region of tissue is described, the tissue having internal and external surfaces. The device includes a first portion for positioning at one of the internal and external surfaces for applying a treatment force to the defect to treat the defect. In addition, the device has a second portion for applying a counter-force, i.e. a biasing force substantially in opposition to the force exerted by the first portion, where the second portion is operable to be positioned so that the biasing force is applied on the other of the internal and external surfaces. In addition, the device includes a coupling member for connecting the first and second portions.

The device is configured to allow the treatment force to be applied at one of the internal and external surfaces against the defect while the biasing (i.e. counter) force is applied at the other of the internal and external surfaces at a location sufficiently distanced from a region of tissue containing the defect so as to substantially avoid application of force at the region of tissue containing the defect.

In a more specific configuration, the device has an inner portion, an outer portion and a coupling member for connecting the inner and outer portions. The inner portion is capable of being positioned internal to the tissue without contacting an inner surface of the region of tissue at the defect. In some embodiments, the inner portion is operable to engage a region of tissue that is spaced apart from the defect, whereas the outer portion is positionable at an outer surface of the tissue at the defect. The coupling member allows for the application of force between the outer and inner portions such that a force is applied against an outer surface of the tissue at the defect by the outer portion, while the inner portion does not substantially apply a force against an inner surface of the tissue at the defect.

In one broad aspect, embodiments of the present invention comprise a device for treating a defect in a vertebral disc. Included in the device are:

(a) an outer portion being positionable at an outer surface of a disc annulus at the defect;

(b) an inner portion being anchorable within a nucleus pulpous substantially without contacting an inner surface of the disc annulus at the defect; and (c) a coupling member for applying a force between the outer portion and the inner portion, such that the outer portion is forced against the outer surface at the defect while the inner portion does not substantially apply a force to the inner surface at the defect.

In some embodiments, the inner portion comprises two members.

In some embodiments, the inner portion is configured to apply an outward force on an inner surface of the disc annulus substantially spaced apart from the defect, when a pulling force is applied by the coupling member.

In some embodiments, the inner portion comprises two arms, the two arms being moveable between a retracted position and an expanded position.

In some embodiments, the two arms comprise a resilient material.

In some embodiments, the arms have substantially atraumatic edges.

In some embodiments, the arms have substantially curved edges.

In some embodiments, the inner portion in an expanded configuration has a substantially heart-shaped configuration.

In some embodiments, the arms comprise a rounded wire having a coating.

In some embodiments, the arms have a length of between about 1 cm to about 3 cm in the retracted position, and wherein tips of the arms are separated by a span of between about 0.5 cm to about 3 cm in the expanded position.

In some embodiments, the arms have a length of about 2 cm in the retracted position and wherein tips of the arms are separated by a span of about 1.5 cm in the expanded position.

In some embodiments, the arms in the expanded position are configured to engage an inner surface of the disc annulus when positioned within the disc nucleus.

In some embodiments, the arms are configured to engage an inner surface of the disc annulus on substantially opposite sides of the defect.

In some embodiments, the outer portion is configured and sized to substantially cover a herniated region of the intervertebral disc.

In some embodiments, the outer portion comprises one or more sutures.

In some embodiments, the outer portion comprises a suture loop operable to be secured to the disc annulus.

In some embodiments, the outer portion is configured to be substantially embedded within outer layers of the disc annulus when the force is applied by the coupling member.

In some embodiments, the outer portion comprises a unitary structure.

In some embodiments, the outer portion has a substantially plate-shaped configuration.

In some embodiments, the outer portion has a width of between about to 2 mm to about 7 mm, a height of between about 1 mm to about 6 mm, and a thickness of between about 0.1 mm to about 0.9 mm.

In some embodiments, the outer portion has a width of about 5 mm, a height of about 4 mm and a thickness of about 0.5 mm.

In some embodiments, the outer portion is asymmetrical.

In some embodiments, the outer portion is foldable.

In some embodiments, the device comprises one or more anchors for securing the outer portion to the disc annulus.

In some embodiments, the one or more anchors comprise knots.

In some embodiments, the one or more anchors are operable to engage with an inner surface of the disc annulus.

In some embodiments, the coupling member comprises a unitary structure.

In some embodiments, the coupling member comprises a suture.

In some embodiments, the coupling member comprises a suture for pulling the inner portion radially outwards and further comprises a knot for pushing the outer portion radially inwards forcing the outer portion against the outer surface at the defect.

In some embodiments, the coupling member is adjustable for altering the distance between the outer portion and the inner portion.

In some embodiments, the coupling member comprises a length adjusting mechanism.

In some embodiments, the mechanism is a screw mechanism.

In some embodiments, the coupling member has a length of between about 2 cm to about 4 cm.

In some embodiments, the coupling member has a length of about 3 cm.

In another broad aspect, embodiments of the present invention comprise a system for treating an intervertebral disc. Included in the system are:
- a device comprising an inner portion anchorable within a nucleus pulposus of the disc substantially without contacting an inner surface of the disc annulus at the defect, an outer portion positionable at an outer surface of a disc annulus at the defect, and a coupling member for applying a pulling force between the inner portion and the outer portion, such that the outer portion is forced against the outer surface at the defect while the inner portion does not substantially apply a force to the inner surface at the defect; and
- an introducer for inserting the inner portion into the disc.

In some embodiments, the system further comprises a length adjusting mechanism for adjusting a length of the coupling member.

In some embodiments, the length adjusting mechanism comprises a screwdriver.

In some embodiments, the coupling member is adjustable for altering the distance between the outer portion and the inner portion.

In a further broad aspect, embodiments of the present invention comprise a method for treating a defect within a tissue. The method comprises the steps of:
(a) anchoring an inner portion of a device within a nucleus pulposus of an intervertebral disc substantially without contacting an inner surface of a disc annulus at the defect;
(b) positioning an outer portion of the device at an outer surface of the disc annulus of the intervertebral disc at the defect; and
(c) applying a pulling force between the outer portion and the inner portion, such that the outer portion is forced against the outer surface at the defect while the inner portion does not substantially apply a force to the inner surface at the defect.

In some embodiments, the inner portion is connected to the outer portion prior to, following or during step (a).

In some embodiments, the step of anchoring the inner portion comprises positioning the inner portion within the disc nucleus.

In some embodiments, the step of anchoring the inner portion further comprises deploying anchoring elements forming a part of, or being attached to, the inner portion.

In some embodiments, the inner portion is inserted into the intervertebral disc using an introducer device.

In some embodiments, the method further comprises a step of retracting the introducer device.

In some embodiments, retracting the introducer device causes the inner portion to be anchored within the intervertebral disc, whereby at least a part of the inner portion engages an inner surface of the disc annulus.

In some embodiments, retracting the introducer device causes the inner portion to be anchored within the nucleus pulposus substantially without contacting an inner surface of the disc annulus.

In some embodiments, the step of retracting the introducer device allows the inner portion to move from a retracted position into an expanded position thereby anchoring the inner portion within the intervertebral disc.

In some embodiments, the step of anchoring the inner portion comprises applying force to the inner portion to expand the inner portion within the disc.

In some embodiments, the method further comprises a step of connecting the outer portion to the inner portion via a coupling member.

In some embodiments, a coupling member is pre-attached to the inner portion and is inserted into the disc along with the inner portion.

In some embodiments, the method further comprises a step of manipulating the coupling member.

Device is used prets, manipulating the coupling member comprises adjusting a length of the coupling member to reduce a distance between the inner portion and the outer portion.

In some embodiments, the coupling member applies a pulling force between the outer portion and the inner portion, such that the outer portion is forced against the outer surface at the defect while the inner portion does not substantially apply a force to the inner surface at the defect.

In some embodiments, the coupling member comprises a suture and a knot, and wherein the step of applying a pulling force comprises (i) pulling the inner portion radially outwards using the suture, and (ii) pushing the outer portion radially inwards using the knot and suture, to force the outer portion against the outer surface at the defect.

In some embodiments, the coupling member comprises a screw and wherein the step of manipulating the coupling member comprises actuating the screw.

In some embodiments, the defect comprises a herniation of the intervertebral disc.

In an additional broad aspect, embodiments of the present invention comprise a device for treating a defect in a tissue, the tissue comprising opposing internal and external surfaces. The device comprises:
- a first portion for positioning at one of the internal and external surfaces for applying a treatment force to the defect to treat the defect;
- a second portion for applying a biasing force in opposition to the force exerted by the first portion, the second portion operable to be positioned so that the biasing force is applied on the other of the internal and external surfaces; and
- a coupling member for connecting the inner portion and the outer portion;
- the device being configured to allow the treatment force to be applied at one of the internal and external surfaces against the defect while the biasing force is applied at the other of the internal and external surfaces at a location sufficiently distanced from a region of tissue containing the defect so as to substantially avoid application of force at the region of tissue containing the defect.

In a further broad aspect, embodiments of the present invention comprise a device for treating a defect in a tissue, the tissue comprising opposing internal and external surfaces, the device comprising:

a first portion for positioning at one of the internal and external surfaces for applying a treatment force to the defect to treat the defect;

a second portion for applying a biasing force in opposition to the force exerted by the first portion, the second portion operable to be positioned so that the biasing force is applied on the other of the internal and external surfaces; and a coupling member for connecting the inner portion and the outer portion;

the device being configured to allow the treatment force to be applied in a first direction along the coupling member while the biasing force has at least one force component in a second direction orthogonal to the first direction.

In a still further broad aspect, embodiments of the present invention comprise a device for treating a defect in a tissue, the device comprising:

an inner portion configured for being positioned at least partially at an internal surface of the tissue;

an outer portion configured for being positioned at an external surface of the tissue at a region of tissue containing the defect; and a coupling member for connecting the inner portion and the outer portion;

the device being configured to allow the outer portion to apply a force against an outer surface of the tissue at the defect while the inner portion applies a force against the inner surface of the tissue substantially spaced apart from the region of tissue containing the defect, substantially without applying a force at the region of tissue containing the defect.

In an additional broad aspect, embodiments of the present invention comprise a device for treating a defect within a tissue. The device comprises:

an inner portion configured for being positioned internal to the tissue, and configured to apply a force against an inner surface of the tissue substantially spaced apart from a region of tissue containing the defect;

an outer portion configured for being positioned external to the tissue adjacent the defect; and a coupling member for connecting the inner portion and the outer portion;

the device being configured to allow the outer portion to be biased against an outer surface of the tissue at the defect when the inner portion is biased against the inner surface of the tissue substantially spaced apart from the region of tissue containing the defect substantially without directly affecting the defect.

In some embodiments the defect comprises a tear within a region of the annulus.

In some embodiments the defect comprises a delamination within a region of the annulus.

In some embodiments the defect comprises a substantially sealed discectomy hole.

In some embodiments the defect comprises a substantially sealed discectomy hole that has been sealed using sutures.

In some embodiments the defect comprises a fissure within a region of the annulus.

BRIEF DESCRIPTION OF THE DRAWINGS

FIG. 1 shows a top view of an intervertebral disc;

FIG. 2A is an illustration of components of a device in accordance with an embodiment of the present invention;

FIG. 2B shows a top view of an intervertebral disc including a herniation;

FIGS. 4A and 4B, respectively, show front side and top views of a rectangular outer portion in accordance with an embodiment of the present invention;

FIGS. 5A and 5B, respectively, show front side and top views of an outer portion having substantially chamfered or rounded edges, in accordance with an alternate embodiment of the present invention;

FIGS. 6A and 6B, respectively, show front side and top views of an outer portion having a substantially contoured shape, in accordance with another embodiment of the present invention;

FIGS. 7A and 7B illustrate, respectively, front side and top views of an embodiment of outer portion that is foldable, in accordance with an embodiment of the present invention;

FIGS. 8A and 8B show, respectively, front side and top views of a circular embodiment of an outer portion, in accordance with an additional embodiment of the present invention;

FIGS. 9A and 9B show, respectively, front side and top views of a elliptical embodiment of an outer portion, in accordance with a further embodiment of the present invention;

FIGS. 10A and 10B show, respectively, front side and top views of a substantially hourglass-shaped embodiment of an outer portion, in accordance with an alternate embodiment of the present invention;

FIGS. 11A and 11B show, respectively, front side and top views of a substantially star-shaped outer portion, in accordance with another embodiment of the present invention;

FIGS. 12A and 12B illustrate, respectively, front side and top views of a substantially star-shaped outer portion incorporating a mesh in accordance with another embodiment of the present invention;

FIG. 13A illustrates a front side view of an embodiment of an asymmetrical outer portion 210 in accordance with another embodiment of the present invention;

FIGS. 13B-13C show top views of various embodiments of outer portion shown in FIG. 13A, in accordance with the present invention;

FIG. 14 shows a perspective view of another asymmetric embodiment of an outer portion 210 in accordance with the present invention;

FIGS. 16A and 16B illustrate, respectively, front side and top views of an embodiment of outer portion having a stacked pattern of sutures, in accordance with an embodiment of the present invention;

FIGS. 17A and 17B illustrate, respectively, front side and top views of an outer portion using sutures in accordance with an embodiment of the present invention;

FIGS. 18A and 18B illustrate perspective and top views of embodiments of outer portion comprising a plate as well as an external balloon in accordance with an alternate embodiment of the present invention;

FIG. 19 illustrates a front side view of alternate embodiment of outer portion configured to attach onto the adjoining vertebral bodies in accordance with the present invention;

FIG. 20 illustrates a front side view of an outer portion having protrusions to secure the outer portion to the disc annulus, in accordance with an embodiment of the present invention;

FIG. 21 illustrates a front side view of an embodiment of an outer portion having a mesh-like configuration, in accordance with the present invention;

FIGS. 22A and 22B show, respectively, front side and top views of an alternate embodiment of an outer portion, comprising a concave surface, in accordance with the present invention;

FIGS. 23A and 23B show front side views of an outer portion in accordance with alternate embodiments of the present invention;

FIG. 23C shows a top view of an embodiment of outer portion comprising a concave surface, in accordance with the present invention;

FIGS. 24A and 24B show, respectively, top and front side views of an inner portion in accordance with an embodiment of the present invention;

FIG. 24C illustrates a top view of an alternate embodiment of an inner portion comprising a convex surface, in accordance with the present invention;

FIG. 24D shows a top view of another embodiment of an inner portion comprising arms in accordance with an embodiment of the present invention;

FIG. 24E is a front side view of an alternate embodiment of an inner portion in accordance with an embodiment of the present invention;

FIG. 25 shows a top view of an inner portion comprising a balloon in accordance with an alternate embodiment of the present invention;

FIGS. 26A-26C illustrate front side views of the inner portion in accordance with various embodiments of the present invention;

FIG. 26D illustrates top view of a circular embodiment of an inner portion in accordance with the present invention;

FIGS. 27A and 27B show, respectively, front side and top views of an alternate embodiment of an inner portion that is substantially heart-shaped, in accordance with the present invention;

FIG. 37E further illustrates the inner portion having arms deployed in their expanded position, in accordance with a method embodiment of the present invention;

FIG. 38A shows a perspective view of a device and a method of use in accordance with an embodiment of the present invention;

FIG. 38B shows an inner portion and an outer portion in accordance with an embodiment of the present invention;

FIGS. 39A and 39B show a device and method in accordance with an embodiment of the present invention having an outer portion that comprises suture; and FIG. 40 shows a device and method in accordance with an embodiment of the present invention.

Throughout the Figures, like reference numbers have been used to indicate like features when possible.

DETAILED DESCRIPTION

Figure 3:
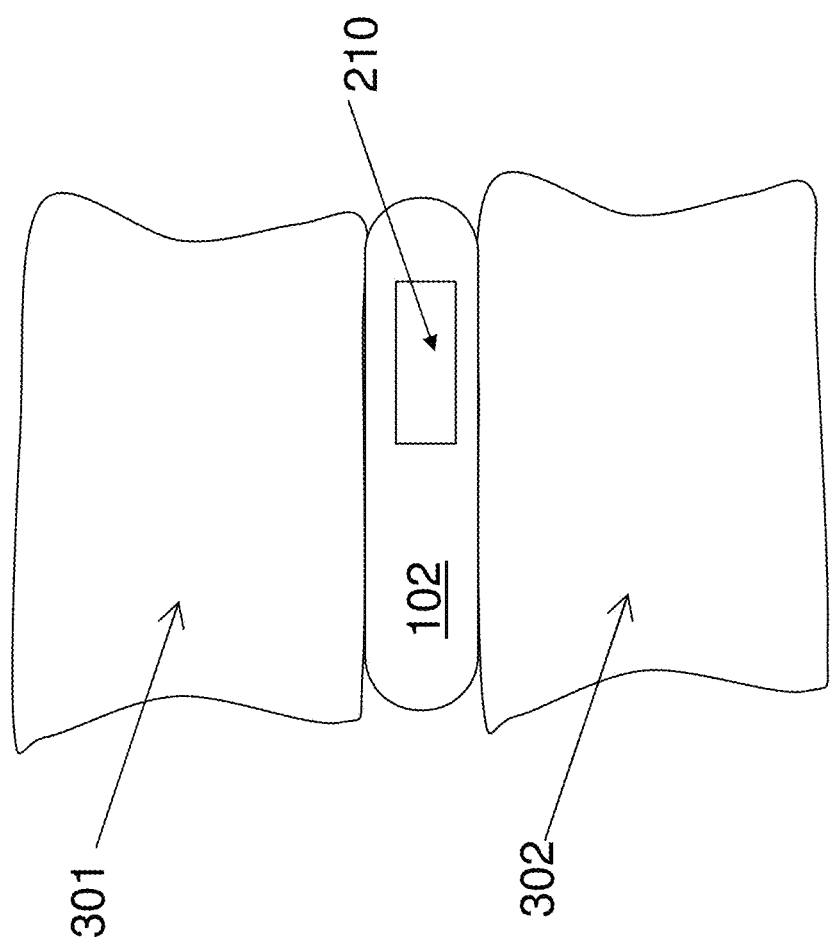
FIG. 3 is an illustration of an outer portion of a device as located external to the annulus of an intervertebral disc, in accordance with an embodiment of the present invention.

With specific reference now to the drawings in detail, it is stressed that the particulars shown are by way of example and for purposes of illustrative discussion of certain embodiments only. Before explaining at least one embodiment in detail, it is to be understood that the disclosure is not limited in its application to the details of construction and the arrangement of the components set forth in the following description or illustrated in the drawings. The various aspects described herein are capable of other embodiments or of being practiced or carried out in various ways. Also, it is to be understood that the phraseology and terminology employed herein is for the purpose of description and should not be regarded as limiting.

The present disclosure describes embodiments for treating a defect in a region of tissue by applying a force at a surface of the tissue containing the defect to treat the defect while a counter-force is applied away from the region of tissue containing the defect, such that the counter-force is substantially not applied at the region of tissue containing the defect.

Embodiments of the present invention are directed to a device for treating a diseased or damaged portion, or in other words a defect, within a region of tissue. In some embodiments, a device as disclosed herein includes the following components:

a) Outer portion (also referred to, in some embodiments, as a posterior anchor): The outer portion is positionable outside a region of tissue to be treated at an outer surface of a diseased or damaged portion of the tissue. In other words the outer portion is positionable at an outer surface of the region of tissue at the defect. The outer portion is capable of applying a force against the outer surface of the region of tissue at the defect when biased. In other words the outer portion is capable of being forced against the outer surface of the region of tissue at the defect. In some embodiments, this component is stiff enough to be able to push a herniation inwardly without buckling. In others, the component is sufficiently stiff so as to substantially contain the herniation. In some embodiments the outer portion may comprise a suture. As mentioned above, the outer portion comprising a suture is positionable at an outer surface of the tissue at the defect and is capable of being forced against the outer surface at the defect. In some such embodiments where the device is used to treat a defect within the intervertebral disc, the suture-based outer portion is embedded within the outer layers of the annulus.

b) Inner portion (also referred to, in some embodiments, as an interior anchor): The inner portion is positionable within the interior of the region of tissue being treated. It is anchorable therein without contacting the inner surface of the region of tissue at the defect. In one embodiment, the inner portion is configured to engage an inner surface of healthy tissue that is spaced apart from the defect. The inner portion is capable of applying a force against the healthy tissue when biased. In some embodiments, for example when used to treat a herniation of an intervertebral disc, this component is wide enough such that it distributes a compression force on a large area of the healthy (non-herniated) annulus. In one example, the inner portion may be referred to as the interior nucleus anchor. In one specific embodiment, where the device is usable for treating a defect within an intervertebral disc, the inner portion is structured to apply a force against an inner wall of the annulus. In alternate embodiments, the inner portion is anchorable within the nucleus pulposus.

The term 'anchorable' may be understood to mean that when a pulling force is applied, for example by the coupling member, the inner portion substantially resists motion, i.e. maintains a substantially fixed position within the tissue. Put differently, in some embodiments, the inner portion is structured and operable to apply a force against an internal portion of the disc when a pulling force is applied against it. In other words, motion of the internal portion is substantially impeded by internal disc material, for example the inner wall of the annulus fibrosus or the nucleus pulposus, when a pulling force is applied. However, it should be understood that, when there is some laxity in the coupling member, for example when a patient is moving such that forces on the disc are changing, then the inner portion may in fact be able to move and adopt a new shape/configuration. Thus, even though the nucleus pulposus or the inner wall of the annulus substantially impedes the movement of the inner anchor, changes in the disc volume due to, for example, the patient's movement may allow the inner portion/anchor to move and reposition/re-orient itself until it again becomes anchored within the tissue.

c) Coupling member: This component functions to connect the inner and outer portions together, and retains them in a biased position. The coupling member is configured to apply a pulling force between the inner portion and the outer portion such that the outer portion is forced against the outer surface of the region of tissue at the defect, while the inner portion does not substantially apply a force to the inner surface of the region of tissue at the defect. In one embodiment, the coupling member allows the inner portion to be biased against an inner surface of the tissue that is spaced apart from the defect and allows the outer member to be biased against an outer surface of the region of tissue at the defect. In one example, this component functions to connect the inner and outer portions together, and defines the length, i.e. distance, between the inner and outer portions. The length, which in some embodiments is adjustable, is related to the level of compression of the herniation (in embodiments configured for treating herniations) and therefore the tension in the coupling member, as will be clarified further herein below. The magnitude of the compressive force can be inversely proportional to the length of the coupling member in a linear system. In other examples, the exerted force may be a function of a non-linear system. In one example, the coupling member may be a tether. In some embodiments, the coupling member may include more than one component, for example the coupling member may comprise a suture and a knot, where tension applied to the suture functions to pull the inner portion outwardly and where the knot may be slid over the suture against the outer portion to apply force to the outer portion against the defect. In such an embodiment, the suture and knot combination function to pull or draw the inner and outer portions together. Thus, in such an embodiment, the coupling member is understood to include both the suture as well as the knot.

The device may be used to treat a defect within a region of tissue within a patient's body such that it is able to substantially reinforce, contain, compress, stabilize, and/or reduce a defect such as a herniation of an intervertebral disc. The defective/damaged/diseased portion of an intervertebral disc that may be treated may include non-limitingly, one or more of a bulge, herniation, fissure or tear, thinning of the annulus, or degradation of the annulus or thickening of the annulus. Furthermore, embodiments of a method of the present invention may be used to treat/repair any other pathology that would lead one to believe that a herniation is imminent (or any pathology that requires annulus lamina to be compressed), all of which may be understood to be encompassed within the term 'defect'. Additional examples of possible treatment applications are described further herein below.

Treatment as used herein may refer to treatment that is substantially effective at treating the defect. In other embodiments the device may be at least partially effective at treating the defect. In an example, treatment may comprise the use of the device to slow down or retard the growth of a herniation. Treatment may also include embodiments where the device is used pre-emptively within a region of tissue to treat an area of tissue that has a risk of developing into a defect. In some cases the 'defect' means the defect itself (for example in the case of a herniation), while in other cases it may mean a region of the defect, i.e. a region of tissue containing, damaged by or affected by the defect (for example, in case of a tear/fissure in the annulus or a repaired discectomy).

A region of the defect (or 'a region of tissue at the defect') includes, at least, tissue substantially surrounding a defect. For example, in embodiments wherein the defect comprises a herniation, the defect (or region thereof) may be defined as the region of tissue having a dimension, for example a radius, that deviates from the radius of the healthy tissue adjacent to and surrounding the defect. More specifically, for illustrative purposes, a herniated intervertebral disc 100 is shown in FIG. 2B, where the healthy tissue is defined as tissue wherein the radius r of the tissue measured from a center-point M within the disc 100 remains constant (within a local area of the disc). For example, the inner wall of the annulus within a local area of the disc 100, such as within a posterior corner of the disc has a substantially constant radius r from the centre point M when healthy. A diseased or herniated portion 103 of the disc has a radius r" that deviates from the radius r in the healthy state. A hernia can thus be understood to be a portion of the annulus 102 that deviates from the baseline radius r, i.e. has a distance from the centre-point that is greater than the normal distance r. Thus, in this example, a "region of a defect" or "defect" is the region of the annulus having a deviation from the normal radius r measured from the centre-point. In other words, with respect to such a herniation, a deviation from the normal or standard distance or radius would be considered a diseased or defective region of the tissue.

In such an embodiment, substantially no force is applied directly by the inner portion to this diseased or defective region of the tissue, i.e. the region of the annulus that has a deviated radius r". Rather, the inner portion in accordance with an embodiment of the present invention, applies a force to region of tissue that has a normal or original radius r. Typically, in embodiments of the present invention, force is applied to healthy tissue, and in the case of a herniation, healthy tissue can be understood to be the regions of the annulus 102 where the original distance or radius r from the centre-point is maintained. Studies have shown that a mean transverse length t at the herniation at vertebral levels L3-4, L4-5 and L5-S1 is about 8 mm to about 12 mm. Thus, in some embodiments, the inner portion is used to apply a force to tissue outside of this range.

In order to determine which region of the disc annulus 102 is at the original radius r and which region of the disc is herniated, a physician may look at the vertebral bodies above and below the disc 100 as they are similarly sized and proportioned to disc 100 and, therefore, a measurement of their diameter can be used to determine what the original radius r of the disc annulus 102 is and a portion of the disc annulus that extends radially beyond this radius r can be determined to be the diseased or herniated region 103. As another example, in order to determine which region of the disc 100 is herniated, the physician may look at discs at the adjacent levels, i.e. look at the discs immediately above and below the disc 100 which have substantially the same shape to determine the normal diameter or radius r of the disc 100. The discs immediately adjacent the disc 100 have substantially the same diameter or radius as disc 100. Thus, the region of disc 100 having a greater radius r" than the normal radius r as determined may define the diseased or herniated portion of the disc.

Device

FIG. 1 shows a top view of an intervertebral disc 100, including a nucleus pulposus 101 in substantially the center of disc 100, as well as a annulus fibrosus 102 which, in a typical healthy disc 100, substantially surrounds nucleus 101.

In accordance with an embodiment of the present invention device 200 comprises: (i) an outer portion 210, as illustrated in FIGS. 6A and 6B, respectively, which show front side and top views of an outer portion 210. The outer portion 210 is configured for interacting with a defective, damaged or diseased area of tissue such as disc 100. Outer portion 210, in some embodiments, is configured to substantially cover at least part of the defective tissue (which may or may not be a herniation) such that at least a part of the defective tissue is located (spatially) between outer portion 210 and inner portion 220. Furthermore, the outer portion 210 is biasable against an outer surface of the defective portion of tissue such as annulus 102 in a radially inward direction. In one example, the outer portion 210 is configured to apply a normal, or substantially perpendicular, force to the surface of the defective tissue (such as the annulus) or compresses the defect inwardly (in a radial direction). The outer portion 210 as shown in FIGS. 6A-6B has a substantially contoured shape. Outer portion 210 of such an embodiment may more readily conform to certain areas of the region of tissue being treated, such as the annulus 102.

The device 200 further comprises: (ii) an inner portion 220 as shown in FIGS. 27A-27B which show, respectively, front side and top views of an embodiment of inner portion 220, whereby inner portion 220 is substantially heart-shaped having arms 221. In an alternate embodiment the device 200 comprises an inner member 220 as shown in FIG. 24D which shows a top view of the inner portion 220 comprising arms 221 which, when deployed within the interior of the region of tissue such as nucleus, engage healthy tissue to which force can be applied. In addition, the embodiments illustrated in FIGS. 24A-24E further comprise curled or curved edges which are directed away from the tissue such as annular wall, in order to avoid piercing the tissue. FIG. 24E is a front side view of an embodiment of inner portion 220 that, in addition to arms 221 also comprises legs 222 that may be used to secure inner portion 220 to tissue above and below the region of tissue being treated such as endplates above and below the herniated disc. In some embodiments the arms may comprise a flexible material. In other embodiments the arms may be relatively stiff.

Inner portion 220 functions to distribute force to non-defective, i.e. healthy, parts of the region of tissue being treated which for example non-limitingly may be an annulus of an intervertebral disc. Structurally, at least a part of inner portion 220 extends away from the defective tissue when anchored within the interior of the region of tissue. For example, some embodiments of inner portion 220 may comprise rigid, semi-rigid or resilient biasing arms that are deployable between a retracted position and an expanded position whereby, upon expansion, the arms are configured extend away from the defective tissue and engage healthy tissue. In some embodiments, inner portion 220 has a relatively large surface area compared to outer portion 210 in order to reduce the pressure on the healthy tissue. Thus, in some embodiments, inner portion 220 distributes force to a healthy portion of a tissue of the annulus while, in alternate embodiments, the force is distributed along the top and bottom of the disc, i.e. at the bony endplates of the adjacent vertebral bodies whether penetrating such structures or not.

As shown in FIG. 27B, the arms 221 may engage a larger surface area of healthy tissue. Similarly, as shown in FIG. 24D, arms 221 of the inner portion 220 when deployed within the interior of the region of tissue being treated may engage healthy tissue to which force can be applied. For example, arms 221 when deployed within the interior of a region of tissue being treated may engage a healthy region of the tissue.

The healthy region of the annulus mentioned above may be a region of tissue that is substantially healthy or substantially free from disease. In other words, the region of tissue is relatively healthy compared to the diseased portion of the disc. The healthy tissue may be more capable of withstanding the force exerted by the inner member than the diseased portion of the disc. In some embodiments, the force exerted by the inner member may be distributed over an area that is substantially larger/wider than the herniation allowing force to be spread over a larger area (thereby reducing the forces applied at any one given location), hence minimizing damage healthy region of tissue.

The device 200 further comprises: (iii) a coupling member 230 that functions to connect the inner 220 and outer 210 portions in a way that allows for the application of outward force by inner portion 220 to cause coupling member 230 to pull the outer portion inwardly. In other words, coupling member 230 comprises an elongate member that is operable to connect inner portion 220 to outer portion 210 and which allows for the transmission of force from the outer portion 210 to inner portion 220. The coupling member 230 functions to pull inner portion 220 and outer portion 210 closer together, thereby increasing the force applied by arms 221 to the healthy region of tissue and concurrently increasing the force with which outer portion 210 is biased against the defect.

In one embodiment, the device 200 has a length of between about 2 cm to about 4 cm (which may define the length of the coupling member or the length of the entire assembled device, i.e. from the proximal edge of the outer portion to the distal edge of the inner portion). In one specific example, the device 200 has a length (L) of about 3 cm. In one embodiment as shown in FIG. 38B, the outer portion 210 comprises a substantially plate-shaped configuration. In some embodiments, the outer portion 210 has a width (w) of between about to 2 mm to about 7 mm, a height (h) of between about 1 mm to about 6 mm, and a thickness (t) of between about 0.1 mm to about 0.9 mm. In one specific example, the outer portion has a width (w) of about 5 mm, a height (h) of about 4 mm and a thickness (t) of about 0.5 mm. In one embodiment, as shown in FIG. 38B, the inner portion 220 has arms having a length (L) that is between about 1 cm to about 3 cm, in the retracted position. The arms have a span (S) of between about 0.5 cm to about 3 cm in the expanded configuration as shown in FIG. 38A. In one specific example, as shown in FIG. 38B, the arms have a length of about 2 cm and run fully parallel to the body in the retracted position. During expansion, the proximal portions of the arms are pushed towards the fixed distal ends such that the arms are bent outwards (resembling a butterfly). When compressed or anchored within the disc, in one example, the proximal ends of the arms are about 0.5 cm from their respective distal ends (In some embodiments this distance (s) may be between about 0 cm to about 1 cm). In the illustrated example, the arms have a span of about 1.5 cm, measured from the proximal end of one arm to the proximal end of the other arm, in the compressed position (i.e. following expansion and compression within the disc). The arms aren't fully bent so as to retain some of their elastic force. In some embodiments, the arms are fabricated from round wire and coated to increase their surface area (prevent cutting of tissue). In one example, as shown in FIG. 38A, the outer portion 210 comprises sutures 212 having anchors 214 embedded within/engaged with the annulus 102. A sliding locking knot (k) may be provided with two ends shown for cinching and locking.

System

Embodiments of a system as disclosed herein comprise a device 200 as described herein, as well as an introducer 300 (which may also be referred to as cannula 300). Some embodiments further include a length adjusting mechanism for adjusting a length of the coupling member. In some such embodiments, the length adjusting mechanism comprises a screwdriver.

The device in accordance with an embodiment of the present invention may be delivered using a cannulated system, which may help reduce the risk of injury to neural structures during implantation within the intervertebral disc as well as post-implantation.

Usage

In one embodiment, the device 200 of the present invention is used to treat a herniation within a region of tissue. In one specific example, the device 200 may be used to treat a herniation within an intervertebral disc. A herniation of the disc may involve bulging of the disc such that a segment of the disc protrudes out as shown by herniation 103. The herniation 103 may be focal or broad involving a wider portion of the disc. In some embodiments, the device 200 may be used to treat a herniation along the posterior aspect of the annulus. Due to the proximity of the posterior aspect of the disc to sensitive neural structures, a herniation 103 along the disc posterior may cause compression of the adjacent neural structures which causing pain. Thus, the diseased portion of the annulus of the herniated disc may not itself be painful (i.e. it may not be the primary pain generator), but pain may be generated when the herniation 103 presses/impinges against neural structures. Thus, it is beneficial to provide a device 200 that may reduce, stabilize or prevent the further growth of a herniation.

In one embodiment, the outer portion may be positioned adjacent an exterior wall of the annulus fibrosis 102 at a diseased or damaged portion of the disc, for example at a herniation 103. The inner portion 220 is positioned within the interior of the disc 100 for example within the nucleus pulposus 101 of the disc 100. In one embodiment, the inner portion 220 engages a healthy region of the inner annulus wall that is spaced apart from a damaged portion of the disc for e. g. a herniation. The inner portion 220 is biased to apply a force, such as a compressive force against the healthy region of the inner annulus wall. The coupling member allows the inner portion to be biased against a region of the inner annulus wall that is spaced apart from the herniation, and further allows the outer portion to be biased against the damaged portion of the annulus. The inner portion does not substantially apply a force against an inner surface of the annulus at the defect, for example a herniation. This may prevent aggravation of the defect and may help prevent the disease or damage to tissue from worsening.

Figure 34:
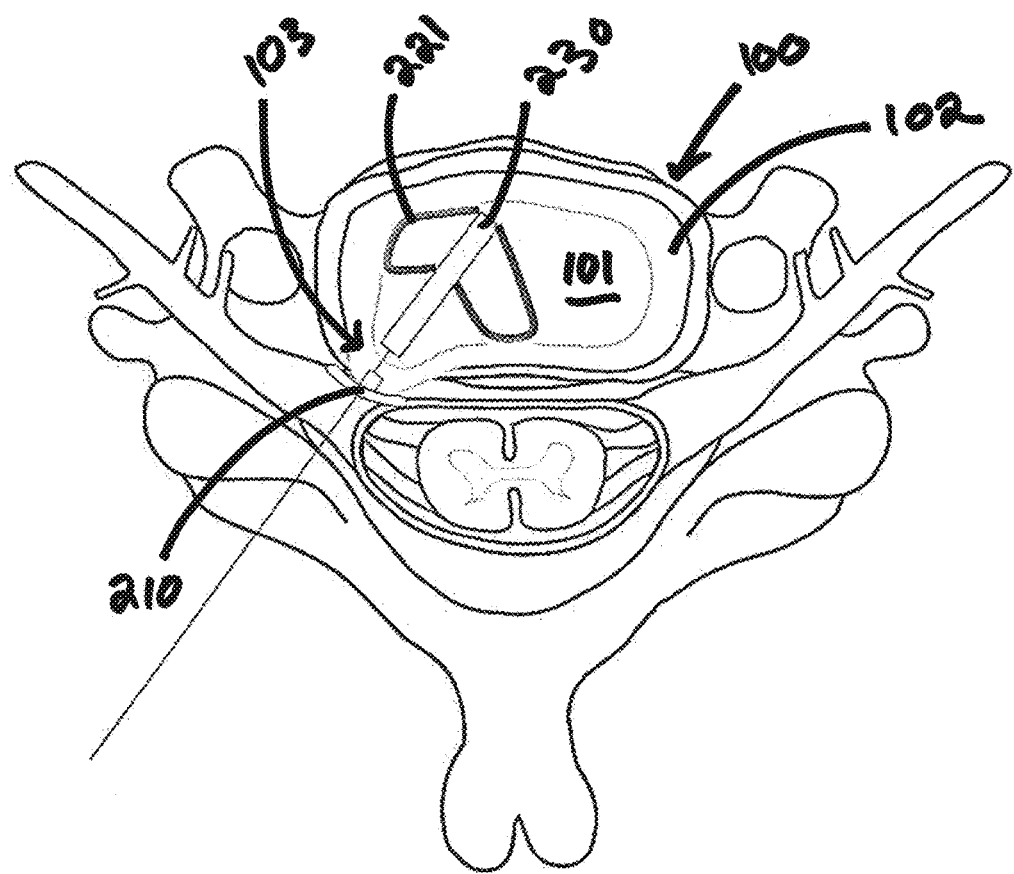

FIG. 34 shows an intervertebral disc 100 including a herniated portion 103 in a posterior side of annulus 102. In addition, FIG. 2 schematically illustrates the primary components of an embodiment of a device 200 of the present disclosure as discussed above, including an outer portion 210, an inner portion 220 and a coupling member 230. As shown, outer portion 210 is configured to reside outside annulus 102, while inner portion 220 is configured for residing within nucleus 101. For clarity, residing outside the annulus should be taken to include embodiments where at least a part of outer portion 210 is embedded somewhat within one or more outer layers of annulus 102. Similarly, residing within the nucleus should be taken to include embodiments where at least a part of inner portion 220 is embedded within one or more inner layers of annulus 102.

As mentioned above, in one embodiment the device 200 functions to contain and/or reverse (i.e. push-in) a defective/damaged/diseased portion of tissue, for example a herniation of an intervertebral disc. In some embodiments, such a procedure may be used instead of a procedure whereby material is removed from the disc, such as a discectomy. In other embodiments, device 200 may be used post discectomy after the hole created within the annulus wall by the discectomy procedure has been closed/repaired such as by tissue re-approximation for example by the use of sutures. As will be described in greater detail hereinbelow, in some embodiments, outer portion 210 is biased against a diseased portion, such as a herniation, to either contain a portion of the herniation or to push it back into the disc. The biasing force is provided by the inner portion 220, at least a part of which is anchored within the nucleus and is configured to apply an outward force against a healthy region of the annulus, such as an inner wall of the annulus that is substantially spaced apart from the damaged region of the annulus. In other words the inner portion 222 is positioned within the nucleus and engages a portion of the inner annulus wall spaced apart from the damaged region. Coupling member 230 connects outer portion 210 and inner portion 220 in a manner such that a force applied by inner portion 220 onto a healthy region of the inner wall of the annulus is countered by the force applied by outer portion 210 onto a portion of the herniation. This distribution of forces may result in an unequal force exerted at the herniation which may cause it to displace inwardly. In other words, a greater local force may be applied by the outer portion 210 against the herniation compared to the local forces applied by the inner portion 220 against healthy regions of the inner wall which may be distributed over a larger area. This may cause the outer portion 210 to displace the herniation inwardly or at least allow the outer portion 210 to resist at some level the further protrusion of the herniated portion of the annulus. The biasing force may be provided via a push-pull approach (i.e. 'pulling' on the inner portion causes the outer portion to 'push' inwardly) or via a tether approach, as is described further hereinbelow.

Thus, if coupling member 230 is adjusted so that its length is reduced, a greater amount of force is applied by inner portion 220 onto a healthy region of the annulus and a substantially equal but opposite force is applied by outer portion 210 onto the herniation. Put differently, inner portion 220 is configured to apply an outward force on an inner surface of the disc annulus thereby pulling coupling member 230 inward and biasing outer portion 220 against an outer surface of said disc annulus.

One embodiment of a method aspect of the present invention includes the following steps: anchoring an inner portion of a device within a disc nucleus of the intervertebral disc; positioning an outer portion of the device over an outer surface of a disc annulus of the intervertebral disc; and biasing the outer portion against the outer surface of the disc annulus using the inner portion, thereby treating the intervertebral disc.

In some embodiments, the step of anchoring the inner portion comprises inserting the inner portion within the nucleus such that is resists motion and/or engages healthy tissue from within the nucleus. The healthy tissue may comprise healthy annular tissue or adjacent bony endplates, for example. In addition, in some embodiments, this step comprises applying force to the inner portion to expand the inner portion within the disc. For example, applying force may comprise pulling on the inner portion or it may comprise manipulating the inner portion with, for example, a screw or other adjustment mechanism. In alternate embodiments, the inner portion deploys automatically when inserted into the nucleus in order to become anchored within the nucleus. In yet further embodiments, a material such as nitrogen is transferred to the nucleus prior to anchoring the inner portion within the nucleus, in order to distend the material within the nucleus, to allow for easier placement of the internal portion.

As mentioned previously, in one specific embodiment, the inner portion is structured to apply a force against an inner wall of the annulus. In some embodiments, the inner portion is anchored by the nuclear material. In other words the inner portion for example when pulled by the coupling member, exerts a force against the nucleus pulposus and if the nuclear material is sufficiently viscous and/or rigid (for example in case of diseased/degenerated discs) the nucleus pulposus impedes the motion of the inner portion.

The step of positioning the outer portion of the device comprises, in some embodiments, positioning the outer portion adjacent to damaged/diseased tissue such as a herniation.

The step of biasing the outer portion comprises, in some embodiments, applying force to the inner portion by adjusting the coupling member so that the inner portion 'pushes' against the healthy tissue with which it's engaged. This, in turn, causes the outer portion to 'push' inwardly against the herniation due to the coupling of the inner and outer portions via the coupling member. In alternate embodiments, rather than causing the outer portion to compress the herniation, a tethering (rope-based) mechanism is employed which involves application of external force to put the inner portion (and thereby the outer portion as well) in tension, following which the device maintains the tension rather than applying additional force. For example, a patient may be asked to position himself so that the protrusion of the herniated portion of the disc is reduced. With the patient maintaining that position, a user may employ devices and methods disclosed herein to position the outer portion of the device adjacent the herniation using a tether-like approach so that the outer portion will maintain the size (or the amount the herniation protrudes) of the herniation once the patient changes position. In other words, rather than applying force to compress the herniation, the device instead secures the herniation in place and doesn't permit it to grow. Thus, the treatment effected by this procedure may, in some embodiments, comprise containing or compressing a herniation.

In some embodiments, the method comprises a further step of connecting the inner and outer portions together using the coupling member. In some embodiments, the inner portion and the outer portion are connected prior to the step of anchoring the inner portion. In other embodiments, the inner portion and outer portion are connected following the step of anchoring the inner portion.

In some embodiments, the step of anchoring the inner portion is effected by positioning the inner portion into the disc nucleus and deploying anchoring elements forming a part of, or being attached to, the inner portion. The anchoring elements, or arms, may be automatically deployed or they may be manually deployed, for example using a screwdriver.

Furthermore, in some embodiments, the inner portion is inserted into the intervertebral disc using an introducer device 300. In some such embodiments, the method comprises a further step of retracting the introducer device 300. In some embodiments comprising the additional step of retracting the introducer 300, the step of retracting causes the inner portion to become anchored within the intervertebral disc, whereby at least a part of the inner portion engages an inner wall of the disc annulus or other healthy tissue which may include bone. In some embodiments, introducers can dilate tissue to facilitate entry.

In some embodiments, the method includes a further step of manipulating the coupling member, for example by adjusting a length of the coupling member to reduce a distance between the inner portion and the outer portion. Put differently, the coupling member may be adjusted to increase the force with which the inner portion engages the healthy tissue which, due to the connection of the inner portion to the outer portion, thereby increases the force with which the outer portion engages the herniation. In some embodiments, as described hereinabove, the coupling member comprises a screw. In such embodiments, the step of manipulating the coupling member comprises actuating the screw.

One particular exemplary embodiment of this method aspect is illustrated in FIGS. 28-36 and FIGS. 37A-37E.

Even though the embodiments shown herein illustrate use of a device 200 in a cervical disc, device 200 may be used non-limitingly in discs within other areas such as the lumbar and thoracic areas.

Figure 28:
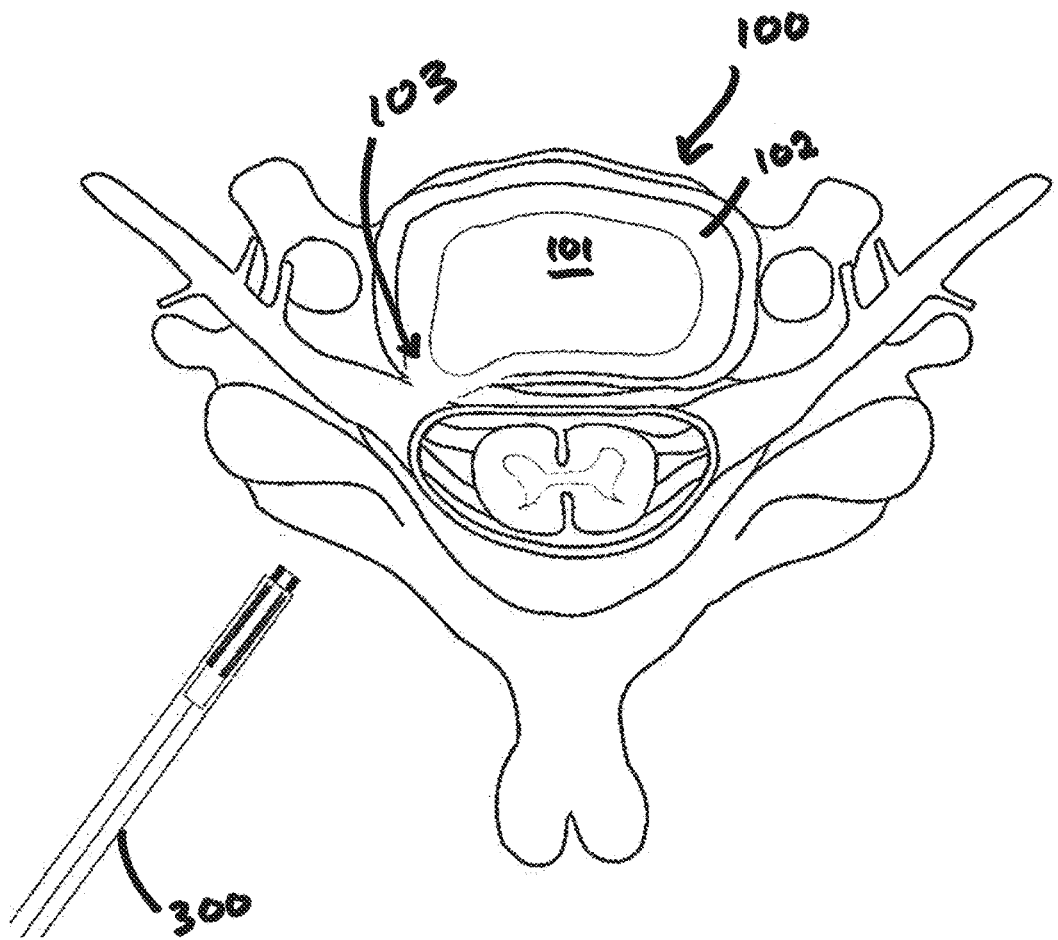
FIGS. 28-31 show steps of inserting an inner portion within a herniated intervertebral disc in accordance with a method embodiment of the present invention.

FIG. 28 shows an introducer 300 approaching an intervertebral disc 100, the disc having a nucleus pulposus 101 and an annulus fibrosus 102. The disc also has a herniated portion 103.

Figure 29:
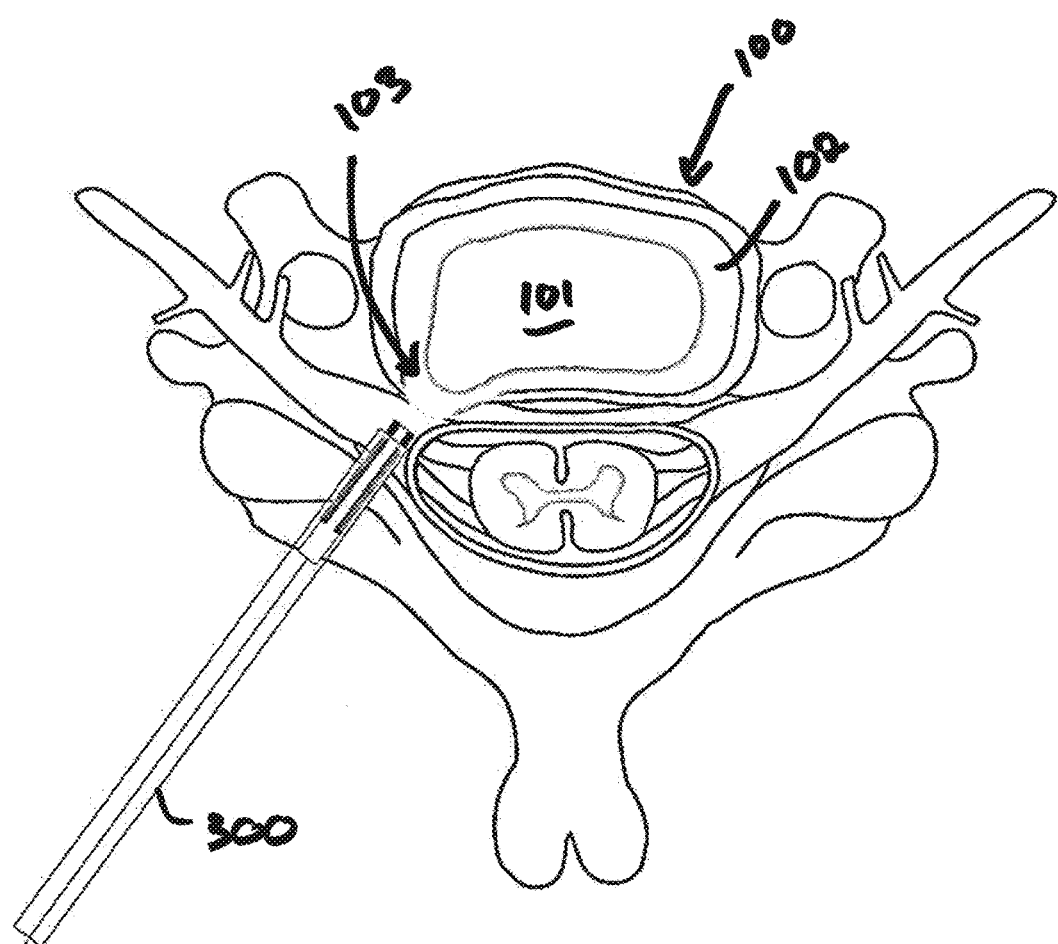

FIG. 29 shows the introducer 300 nearing disc 100, targeting herniated portion 103.

Figure 30:
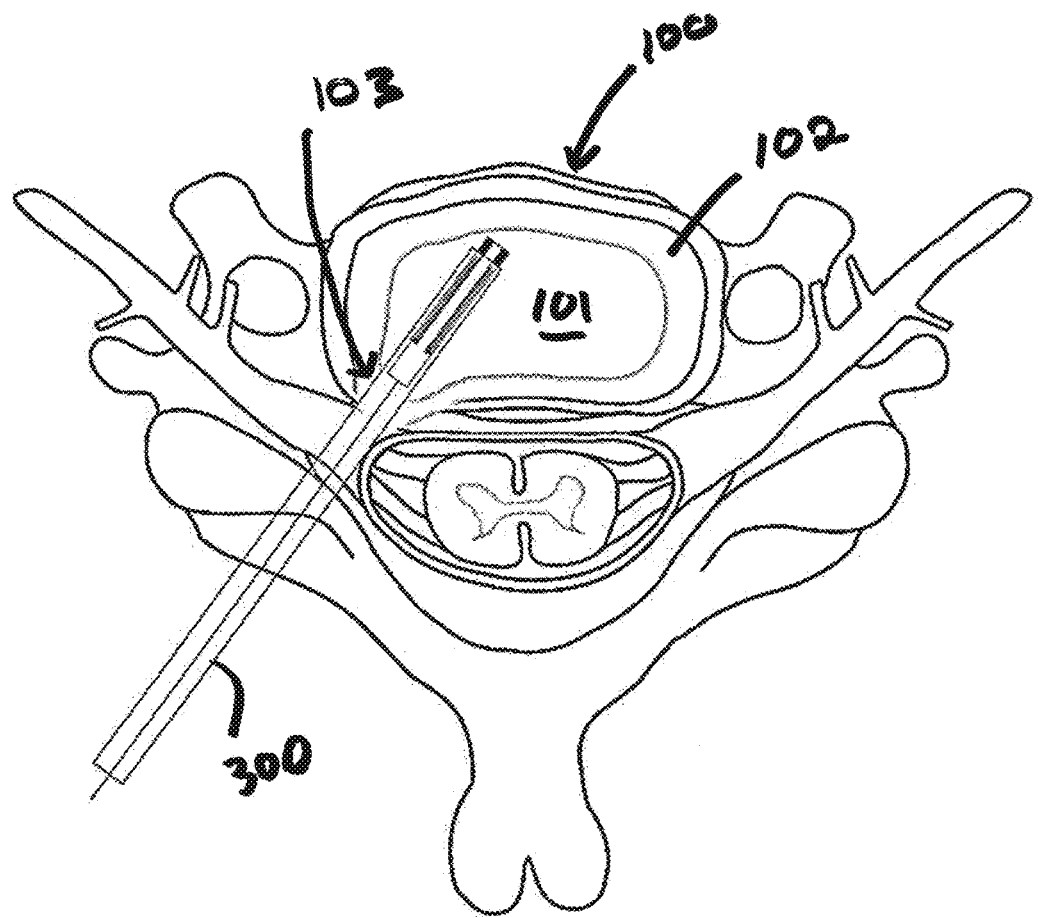

FIG. 30 shows the introducer 300 having entered disc 100 through herniated portion 103. The introducer 300 is shown positioned within nucleus 101.

Figure 31:
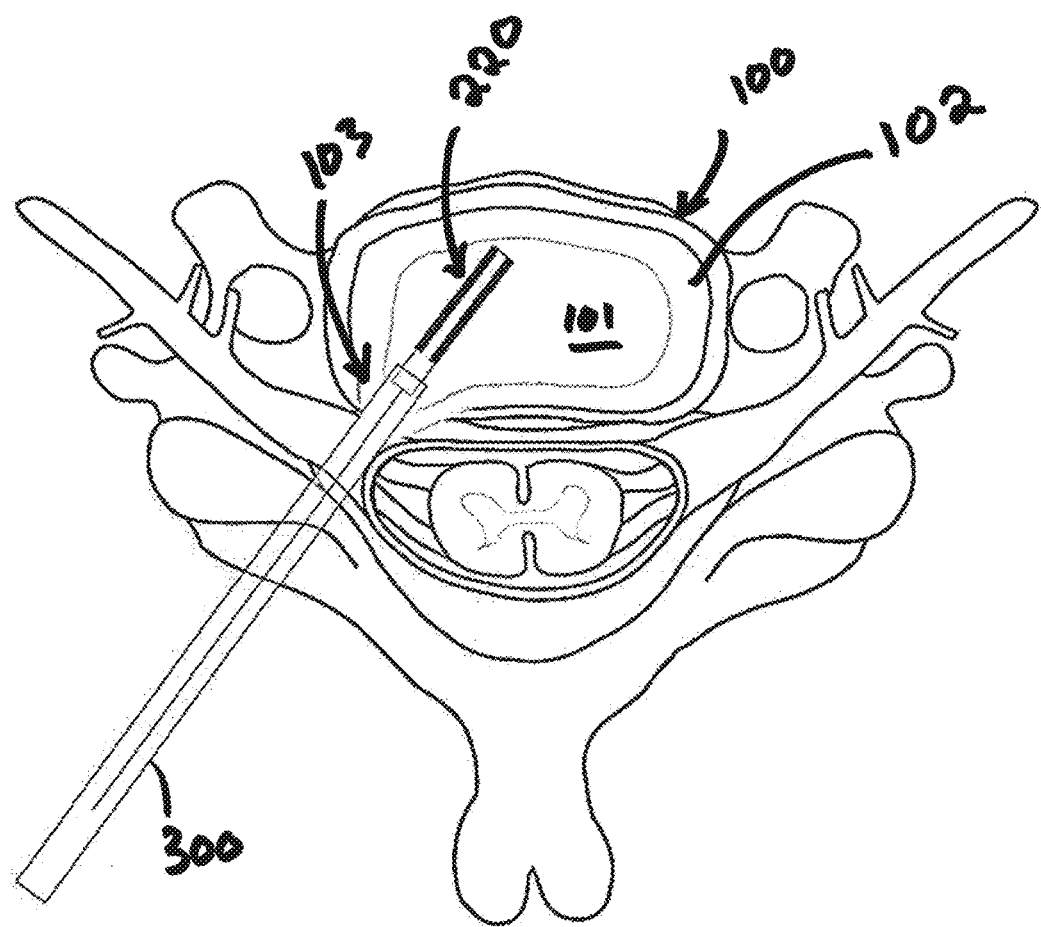

FIG. 31 shows the introducer 300 retracted, exposing internal portion 220 which had been carried within introducer 300.

Figure 32:
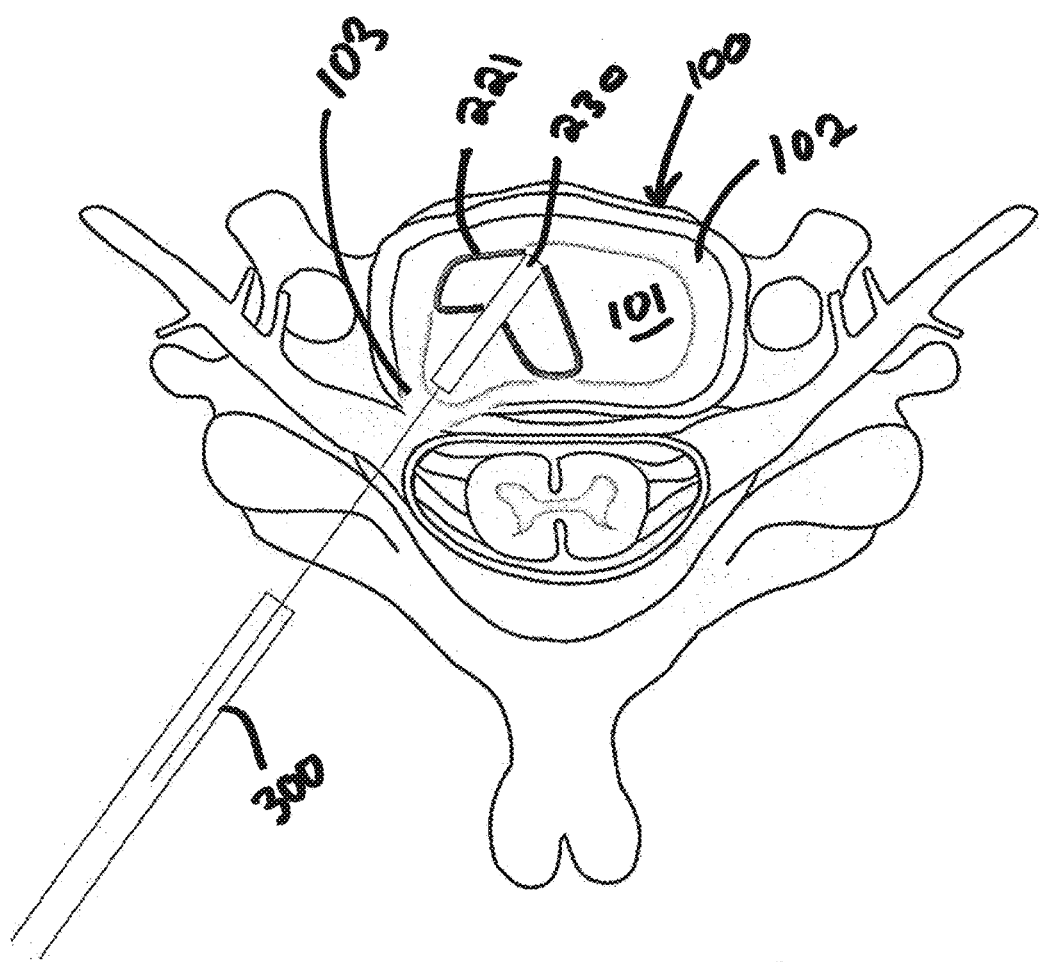
FIG. 32 shows an inner portion in an expanded configuration, within the disc, in accordance with a method embodiment of the present invention.

In FIG. 32, inner portion 220 is shown in an expanded configuration, with arms 221 engaging an inner wall of annulus 102, spaced apart (or located at a distance) from herniation 103. In addition, coupling member 230 is shown connected to arms 221 of internal portion 220. As mentioned hereinabove, arms 221 may be automatically deployed once introducer 300 is retracted, thus exposing arms 221. Alternatively, a user may apply force to expand arms 221 of inner portion 220 to anchor inner portion 220 within the nucleus.

Figure 33:
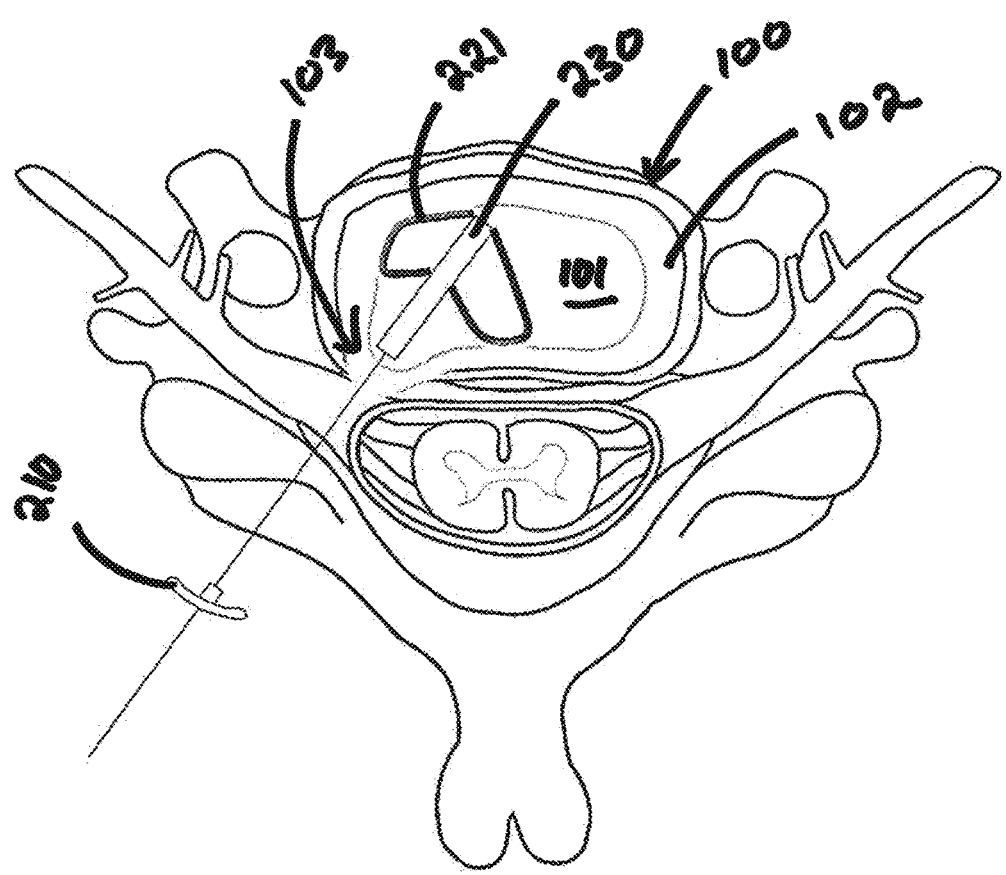
FIG. 33-34 illustrate steps of positioning an outer portion substantially adjacent the herniation, in accordance with a method embodiment of the present invention.
Figure 35:
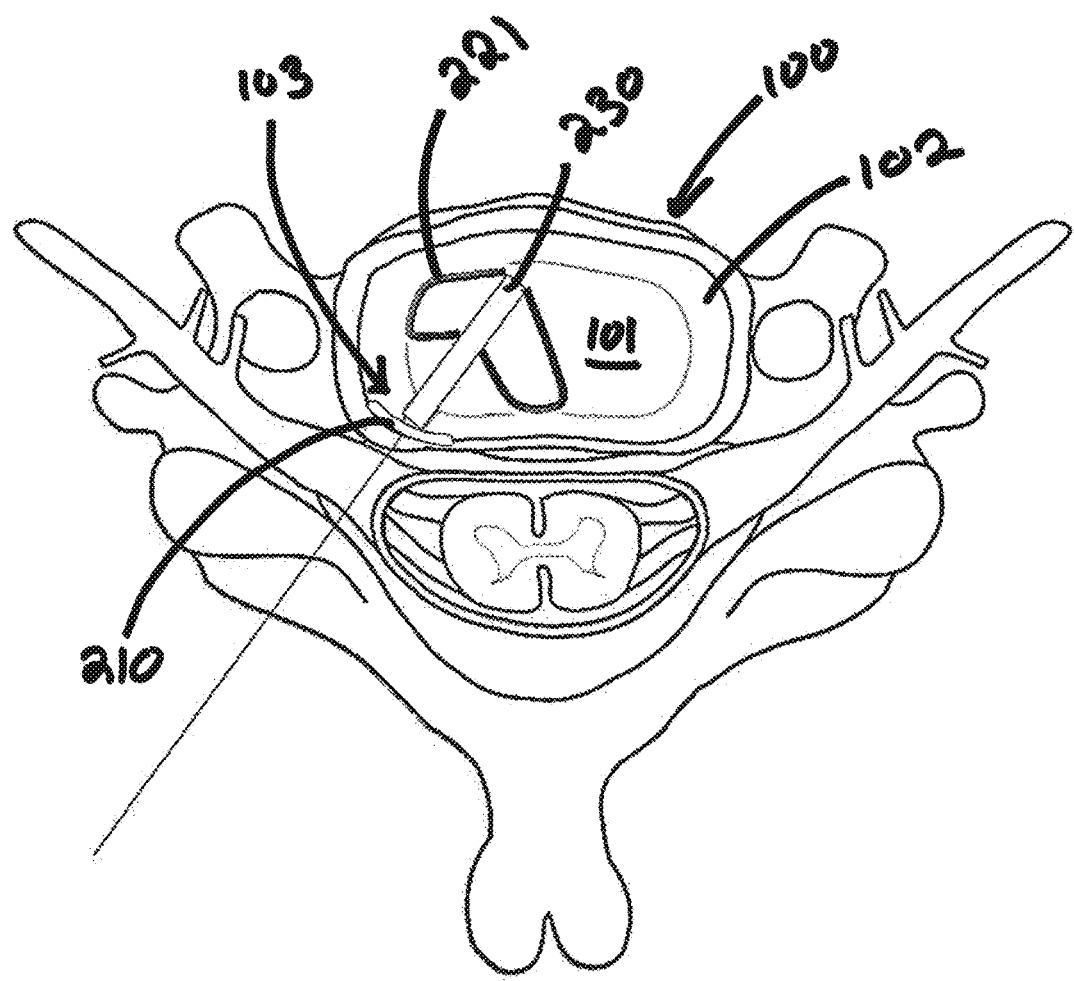
FIG. 35, shows a step of actuating the coupling member to pull inner and outer portions closer together in accordance with a method embodiment of the present invention.

FIG. 33 illustrates outer portion 210 being advanced towards herniation 103 of disc 100 and FIG. 34 shows outer portion 210 positioned substantially adjacent herniation 103. In FIG. 35, coupling member 35 has been actuated, for example, using a screw driver (not shown), to pull inner portion 220 and outer portion 210 closer together, thereby increasing the force applied by arms 221 to the healthy portions of annulus 102 and concurrently increasing the force with which outer portion 210 is biased against herniation 103. As illustrated in FIG. 35, sufficient force has been applied so as to significantly compress herniation 103.

Figure 36:
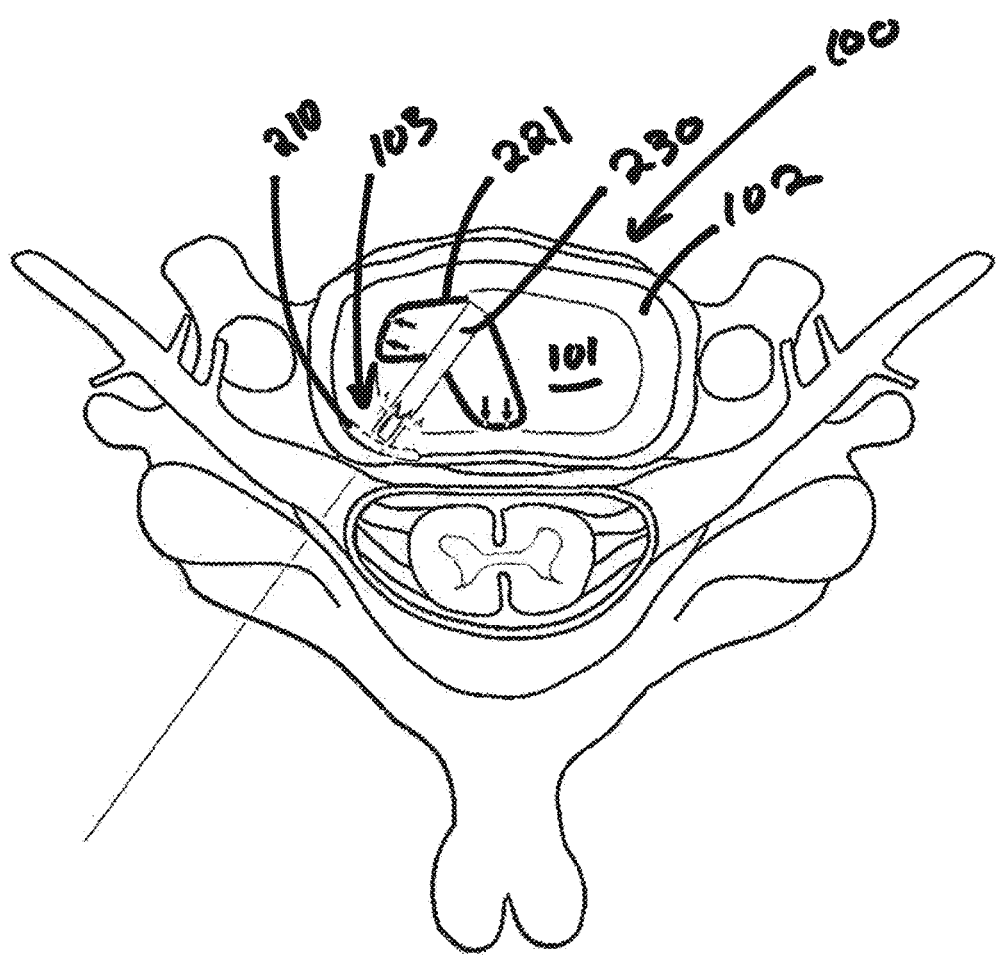
FIG. 36 is a schematic illustration of the directions in which force is being applied when device is implanted, in accordance with a method embodiment of the present invention.

FIG. 36 is a schematic illustration of the directions in which force is being applied when device 200 is implanted. Arms 221 are shown applying force against healthy tissue of annulus 102 while outer portion 210 is shown applying a normal (or perpendicular) force against the herniated portion 103 of annulus 102.

Figure 37B:
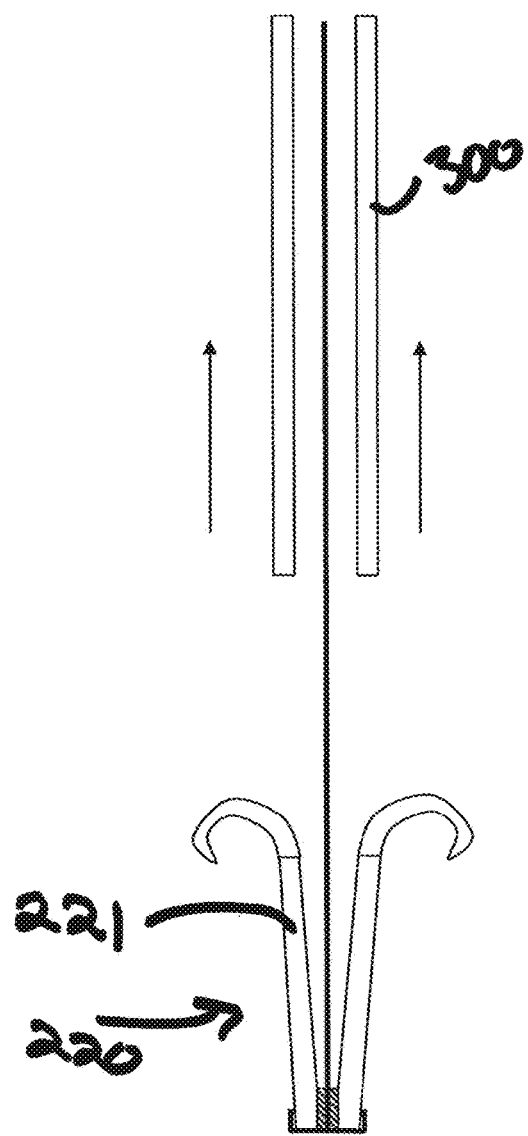
FIG. 37B illustrates delivery of an inner portion comprising arms, into the target tissue by retracting introducer to partially deploy the arms in accordance with a method embodiment of the present invention.
Figure 37A:
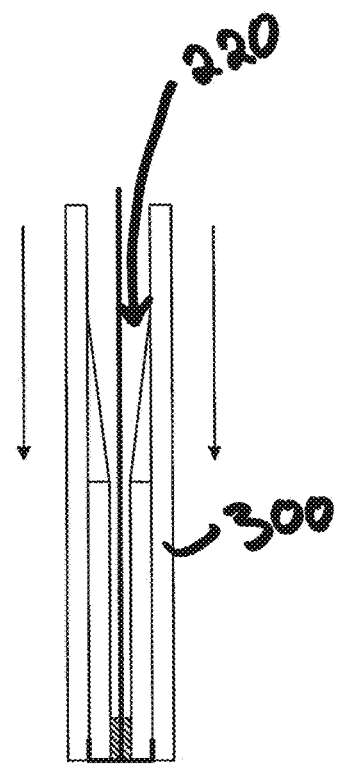
FIG. 37A shows an introducer carrying an inner portion therein, in accordance with a method embodiment of the present invention.
Figures 37C, 37D:
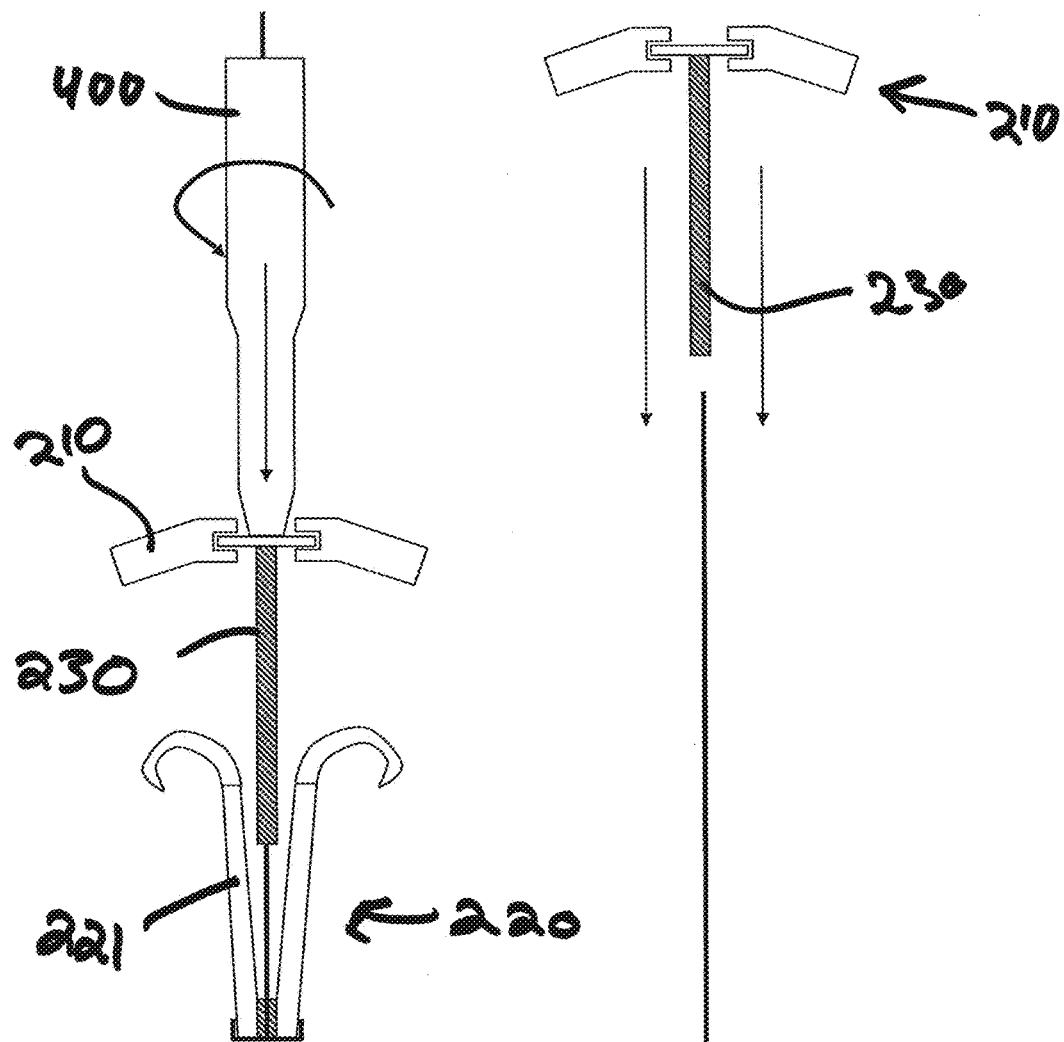
FIG. 37C shows an outer portion to which a coupling member is attached, approaching the inner portion, in accordance with a method embodiment of the present invention.
FIG. 37D illustrates an adjustment mechanism coupled to coupling member, and being actuated to cause the coupling member to advance inwardly until it connects to inner portion thereby connecting outer portion to inner portion, in accordance with a method embodiment of the present invention.

FIGS. 37A-37E illustrate some of the method steps in greater detail. FIG. 37A shows an introducer 300 carrying an inner portion 220 therein. FIG. 37B illustrates delivery of inner portion 220, comprising arms 221, into the target tissue. Introducer 300 has been retracted and arms 221 have been partially deployed as a result. FIG. 37C shows outer portion 210, to which coupling member 230 is attached, approaching inner portion 220. The embodiment illustrated by this FIG. 37C is thus different in this respect from the embodiment illustrated by, for example, FIGS. 28-36 above, as, in this embodiment, coupling member 230 is attached to outer portion 210 prior to implantation whereas, in the embodiment described above, coupling member 230 was attached to inner portion 220 prior to insertion.

Figures 37E, 37F:
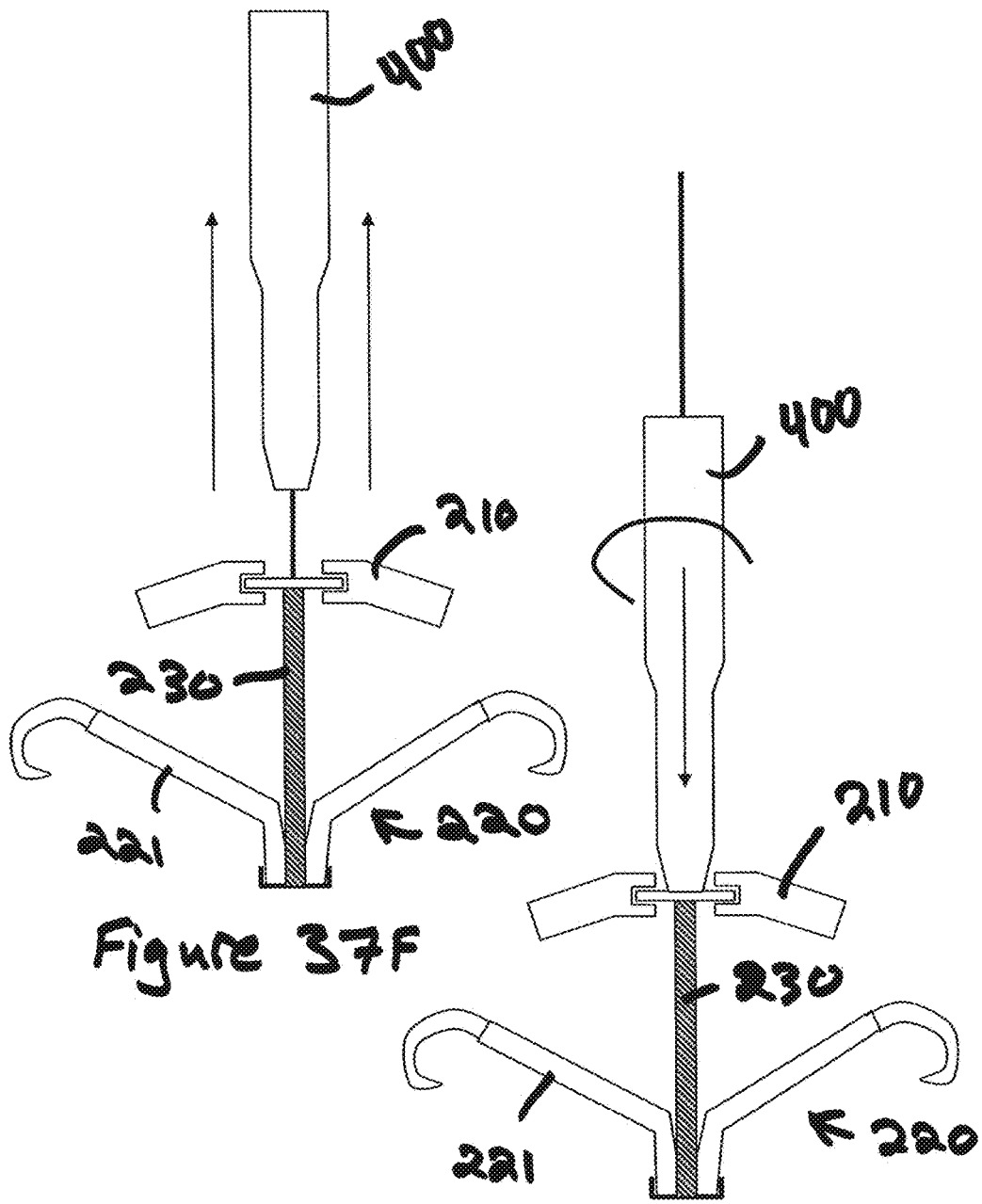
FIG. 37E shows a coupling member connected to the inner portion and thereby connecting the outer portion to the inner portion.
FIG. 37F illustrates an adjustment mechanism being retracted from the implanted device, in accordance with a method embodiment of the present invention.

FIG. 37D illustrates an adjustment mechanism 400, for example a screwdriver, being coupled to coupling member 230, which may, for example, comprise a screw. Adjustment mechanism 400 is actuated (in this case, rotated) to cause coupling member 230 to advance inwardly until it connects to inner portion 220, thereby connecting outer portion 210 to inner portion 220 as shown in FIG. 37E. As coupling member 230 is advanced, arms 221 deploy further until they reach their expanded position as shown in FIG. 37E. Finally, FIG. 37F illustrates adjustment mechanism 400 being retracted from the implanted device.

A specific embodiment of a device of the present invention is shown in FIGS. 39A-39B in use. FIG. 39A illustrates an internal portion 220 similar to that previously described. The arms 221 are deployed by moving the proximal ends of the arms towards the distal end, thereby causing the arms to fold back onto themselves. Notwithstanding any other step described herein below, these arms can be locked in place once deployed within the disc. The proximal portion of the hub to which the arms 221 are attached can have include a suture retaining device 214. Alternatively, a suture retaining device may be attached to the hub. In one particular embodiment, as shown in FIG. 39B, after the internal portion 220 is deployed, the delivery system is withdrawn exposing 4 sutures 212 folded back on each other (which would appear to the user as 8 stitches). The sutures 212 are folded back by "entering" through the outer annular portion of the retaining device and returning through a retaining hole 214' (shown) or through individual exit holes (not shown; in alternate embodiments there may be 4 pairs of holes or more, depending, for example, on the number of sutures used) of the suture retaining device.

Each suture 212 has a retainer end and a 'cinching' end $212x$. After the inner portion 220 is deployed and the sutures 212 exposed, the delivery system deposits the retainer 214 in the desired tissue. After this point, only half of the sutures 212 remain to the user (i.e. the sutures 212 are no longer folded over, so that only one end of each suture 212 remains visible). The remaining visible sutures can be tightened or cinched by pulling on their free ends $212x$. A sliding locking knot K allows the sutures 212 to be tightened and ensures that tension is maintained. Once the desired tension is achieved, the free ends are trimmed to approximately the exterior surface of the annulus 102, such that a length of suture 212 remains proximal from the knot that equals the distance from the suture retaining device to the exterior of the disc.

Alternate Embodiments

In various alternate embodiments, device 200 may comprise various alternatives of an outer portion 210, an inner portion 220 and a coupling member 230 which will be presently described in greater detail.

Outer Portion

FIG. 3 shows an anterior-posterior (A-P) side view of a disc annulus 102 bounded by vertebral bodies 301 and 302. Outer portion 210 is shown located substantially external to annulus 102.

FIGS. 4-14 illustrate various embodiments of an outer portion 210.

FIGS. 4A and 4B, respectively, show front side and top views of a rectangular component 210, which may be fabricated out of a metallic or plastic material such as PEEK, for example and which may be substantially plate-shaped.

FIGS. 5A and 5B, respectively, show front side and top views of an outer portion 210 having substantially chamfered or rounded edges, which may reduce trauma on annulus 102.

As mentioned above, FIGS. 6A and 6B, respectively, show front side and top views of an outer portion 210 having a substantially contoured shape. Such an embodiment may more readily conform to certain areas of annulus 102.

In some embodiments, for example those shown in FIGS. 4-6, outer portion may be formed of one piece of material, i.e. outer portion 210 may comprise a unitary structure.

FIGS. 7A and 7B illustrate, respectively, front side and top views of an embodiment of outer portion 210 that is foldable, for ease of delivery.

FIGS. 8-11 illustrated embodiments of outer portion 210 having various shapes. FIGS. 8A and 8B show, respectively, front side and top views of a circular embodiment of an outer portion 210. FIGS. 9A and 9B show, respectively, front side and top views of a elliptical embodiment of an outer portion 210. FIGS. 10A and 10B show, respectively, front side and top views of a substantially hourglass-shaped embodiment of an outer portion 210. FIGS. 11A and 11B show, respectively, front side and top views of a substantially star-shaped embodiment of an outer portion 210.

Some embodiments of outer portion 210 having a star shape may be inwardly foldable, in an umbrella-like fashion, for ease of delivery/installation. Such embodiments may be fabricated from a material which is soft and/or flexible enough to allow it to be folded in such a manner.

FIGS. 12A and 12B illustrate, respectively, front side and top views of an embodiment of outer portion 210 being substantially star-shaped and incorporating a mesh 211 between the 'legs' of the star.

FIG. 13A is a front side view of an embodiment of an asymmetrical outer portion 210. For example, such an embodiment may increase in height in a lateral (as illustrated in this figure, left to right) or medial direction and may be useful in discs where the disc height varies laterally. FIGS. 13B-13C shows top views of various embodiments of outer portion 210 shown in FIG. 13A. As shown, for example, in FIG. 13C, outer portion 210 may be asymmetrical in more than one direction such it more readily conforms to the contour of the intervertebral disc.

FIG. 14 shows a perspective view of another asymmetric embodiment of an outer portion 210. In the illustrated embodiment, outer portion 210 increases in thickness or width as its height increases. Alternatively, the width of outer portion 210 may decrease as its height increases. Such embodiments may be beneficial to assist in matching outer portion 210 to the anatomy of the endplates of the adjoining vertebral bodies. In alternate embodiments, the thickness or width of outer portion 210 is maximized at substantially mid-height. In further embodiments, the change in thickness occurs in a horizontal, rather than vertical, direction. For example, the width of outer portion 210 may increase towards an edge of the disc where the annulus may be thicker.

FIGS. 15A-17B illustrate embodiments of outer portion 210 which utilize sutures to contain and/or compress a herniation or a portion thereof or a defect or a portion thereof.

Figure 15B:
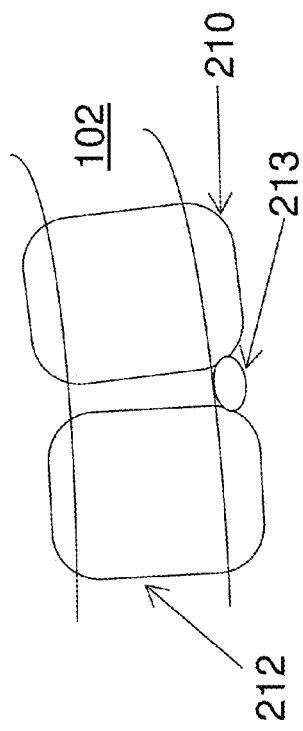
FIGS. 15B-15E show top views of various embodiments of an outer portion utilizing sutures in accordance with various embodiments of the present invention.
Figure 15C:
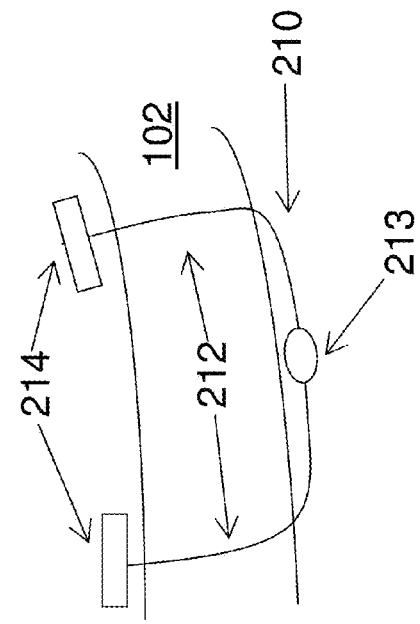
Figure 15A:
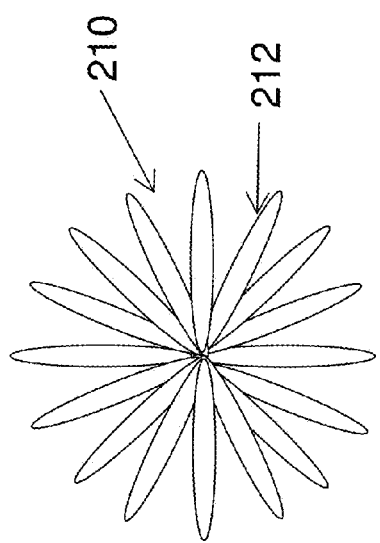
FIG. 15A shows a front side view of outer portion comprising sutures in accordance with an embodiment of the present invention.
Figure 15D:
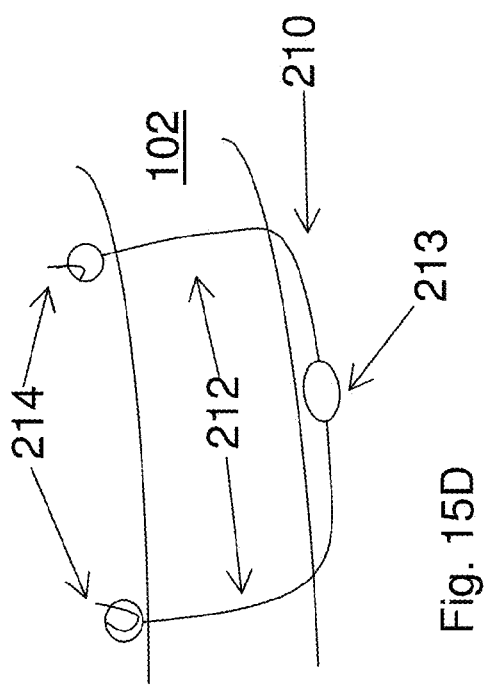
Figure 15E:
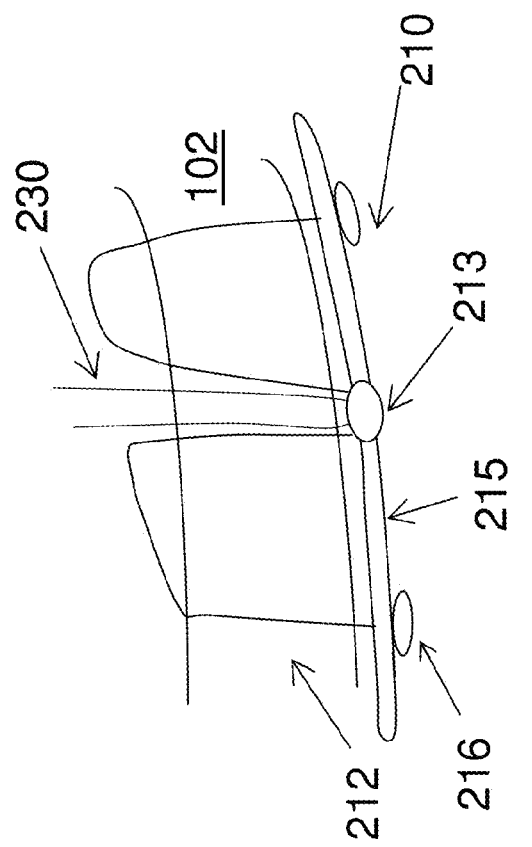

FIG. 15A shows a front side view of an embodiment of outer portion 210 comprising sutures 212 formed into a substantially daisy/flower shape. FIGS. 15B-15E show top views of various embodiments of the outer portion of FIG. 15A. FIG. 15B illustrates suture 212 woven through annulus 102 and back out again to form loops. Sutures 212 are connected to outer portion connector 213, which in turn is connected to coupling member 230 (not shown). FIG. 15C shows sutures 212 woven through annulus 102 and anchored within the nucleus using suture anchors 214, which may comprise metal bars as illustrated herein. In some such embodiments, the anchors 214 are in addition to inner portion 220 which is used to bias the sutures against the herniation. The outer portion 210 may comprise sutures 212 that are anchored within the nucleus against an inner surface of the annulus using suture anchors 214. The sutures anchors may be positioned against an inner surface of the annulus that is substantially spaced apart from the defect. In alternate embodiments, the inner portion 220 may comprise suture anchors 214 positioned against an inner surface of the annulus against healthy tissue substantially spaced apart from the defect. FIG. 15D illustrates a similar embodiment, wherein suture anchors 214 comprise knots. FIG. 15E illustrates an embodiment of outer portion 210 comprising sutures 212 as well as a plate 215. Sutures 212 are secured to plate 215 using support members 216 which may comprise, for example, bars or rods. In such an embodiment, sutures 212 may not directly engage the herniation but may instead apply a force onto plate 215 which in turn spreads this force across the herniation.

FIGS. 16A and 16B illustrate, respectively, front side and top views of an embodiment of outer portion 210 having a stacked pattern of sutures 212 (similar to two columns of pancakes, for illustrative purposes). As shown more readily in FIG. 16B, support members 216 may be oriented substantially vertically to allow for such a stacked configuration. Support members 216 connect to outer portion connector 213 which, in turn, connects to coupling member 230 (shown in dashed outline). Suture anchors 214 may be take various forms as shown hereinabove.

FIGS. 17A and 17B illustrate, respectively, front side and top views of an embodiment of outer portion 210 having a ladder-shaped configuration of sutures 212. As shown in FIG. 17B, an additional suture 212' may be used to tighten sutures 212. In addition, in some such embodiments, sutures 212 may be inserted into annulus 102 such that they cover an area larger than the area of herniation 103.

In alternate embodiments, the sutures may form various other patterns, as befits the particular patient and disc being treated.

FIGS. 18A and 18B illustrate perspective and top views of embodiments of outer portion 210 comprising a plate 215 as well as an external balloon 217 positioned between plate 215 and annulus 102. Balloon 217 may alternatively be replaced by a gelatinous material to allow outer portion 210 to more readily match the contour of the intervertebral disc.

FIGS. 19 and 20 illustrate front side views of alternate embodiments of outer portion 210. In the embodiment of FIG. 19, outer portion 210 is configured to clip onto the adjoining vertebral bodies. In FIG. 20, outer portion 210 comprises protrusions 218 to secure outer portion 210 to the disc annulus.

FIG. 21 illustrates a front side view of an embodiment of outer portion 210 having a mesh-like configuration. Such an embodiment may function to contain the herniation in place rather than compress the herniation back into the disc. The shape of the mesh may be customizable on a patient-by-patient basis. Such an embodiment may be beneficial in that it allows for flexion and rotation of the intervertebral disc. The mesh may comprise a flexible material. In other embodiments the mesh may be relatively stiff.

FIGS. 22A and 22B show, respectively, front side and top views of an alternate embodiment of outer portion 210, where outer portion 210 comprises a concave surface, i.e. it is indented relative to the annulus 102 in order to focus pressure initially on the center of the herniation.

FIGS. 23A and 23B show front side views of alternate embodiments of an outer portion 210. FIG. 23C shows a top view of an embodiment of outer portion 210 that comprises a concave surface, similar to that shown in FIG. 22B, as well as a further indentation to provide even more pressure on the focal point of the herniation.

It should be noted that, in embodiments wherein outer portion 210 is folded for insertion, outer portion 210 may be resilient and may be biased in an open or expanded configuration, such that it automatically unfolds upon positioning (i.e. after a delivery device which had constrained outer portion 210 in the folded configuration is removed/retracted).

Inner Portion

FIGS. 24A and 24B show, respectively, top and front side views of an embodiment of an inner portion 220, showing that inner portion 220 is configured to be larger than the herniation so that a substantial part of inner portion 220 is anchored within the nucleus spaced apart from the area of the herniation. FIG. 24C illustrates a top view of an alternate embodiment where inner portion 220 comprises a convex surface (i.e. protrudes away from annulus) in order to further distance inner portion 220 from the weakened annulus in the area of the herniation.

As mentioned previously, FIG. 24D shows a top view of a further embodiment of inner portion 220 comprising arms 221 which, when deployed within the nucleus, engage healthy tissue to which force can be applied. In addition, the embodiments illustrated in FIGS. 24A-24E further comprise curled or curved edges which are directed away from the annular wall in order to avoid piercing the annulus. FIG. 24E is a front side view of an embodiment of inner portion 220 that, in addition to arms 221 also comprises legs 222 that may be used to secure inner portion 220 to endplates above and below the herniated disc.

FIG. 25 shows a top view of an embodiment of inner portion 220 that comprise an internal balloon 223 which may be inflated/expanded to conform to the shape of the nucleus. Internal balloon 223 may be filled with any suitable material including, for example, air, gel or other fluids and can include nucleus pulposus replacements.

FIGS. 26A-26C illustrate front side views of various embodiments of inner portion 220, while FIG. 26D illustrates top view of a circular embodiment of inner portion 220.

As discussed previously, FIGS. 27A and 27B show, respectively, front side and top views of an alternate embodiment of inner portion 220, whereby inner portion 220 is substantially heart-shaped and whereby arms 221 may engage a larger surface area of healthy tissue.

Coupling Member

In some embodiments, coupling member 230 is adjustable for altering the distance between outer portion 210 and inner portion 220 or for increasing/decreasing the force placed on inner portion 220 and outer portion 210. In some such embodiments, coupling member 230 comprises a length adjusting mechanism such as a screw or ratchet mechanism. Alternatively, coupling member 230 may employ a tethering mechanism to transmit the force between inner portion 220 and outer portion 210.

In some embodiments, coupling member 230 is either integral with inner portion 220 or is coupled thereto prior to insertion of inner portion 220 into the disc. In some embodiments, coupling member 230 is coupled to outer portion 220 prior to insertion such that, for example, device 200 (inner portion 220, outer portion 210 and coupling member 230) comprises a unitary, one-piece device upon insertion.

In alternate embodiments, coupling member 230 is inserted separately from outer portion 210 and is coupled to outer portion 210 during the course of a treatment procedure, for example after outer portion 210 is inserted into the patient's body.

In some embodiments, coupling member 230 is fabricated from material that doesn't stretch/elongate significantly so that it will transmit a force from one end to the other instead of merely stretching.

Additional Features

Some embodiments of device 200 may include components that have one or more coatings, including but not limited to:
Drug-eluting, where the drug/medicament may be:
Anti-inflammatory (steroidal or non-steroidal)
Scar tissue promoting
Annular healing/collagen promoting
Anti-vascularization coating
Anti-innervation
Anti-bacterial (for example, silver)
Hydrophobic/hydrophilic
Heat activated
Sticky or adhesive, to aid in positioning the component of device 200 to which it's attached
Include other means to increase friction with respect to the tissues including surface modifications.
The component may be coated with annular material (or material that mimics the annulus), including but not limited to:
Porcine or Bovine
Human
Collagen-coated material
Material coated with artificial collagen
The component may be coated with bone or a bone-scaffold material if in contact with the vertebral bodies, to promote bony growth and prevent degeneration of the vertebral bodies
The component may be coated with material mimicking ligaments or layers of fascia Further Applications/Uses As an exemplary application, embodiments of devices and methods disclosed herein may be used to reinforce, contain, compress, stabilize, and/or reduce a defect such as a herniation within the intervertebral disc. The herniation may be focal or broad. The defective/damaged/diseased portion of an intervertebral disc may include non-limitingly, one or more of a bulge, herniation, fissure or tear, thinning of the annulus, or degradation of the annulus or thickening of the annulus. In some embodiments, such a procedure may be used instead of a procedure whereby material is removed from the disc, such as a discectomy. In other words, embodiments of a method of the present invention may be utilized to avoid more invasive procedures such as discectomies or disc decompression, whereby disc material is removed from the disc. In other embodiments, device 200 may be used post discectomy after the hole created within the annulus wall by the discectomy procedure has been closed/repaired such as by tissue re-approximation for example by the use of sutures.

In still other embodiments, embodiments of a device of the present invention may be used pre-emptively within a region of tissue to treat an area of tissue that has a risk of developing into a defect. This may include a region of the annulus having a delamination. In the intervertebral disc the annulus wall comprises lamella or layers. These layers or lamella may separate or in other words delaminate from each other. Nucleus pulposus migration may cause fissures or cracks to form within the annulus wall. These may be areas that may develop into a herniation. Thus the device, in accordance with an embodiment of the present invention may be used to cinch the layers together and thus treat the intervertebral disc before a herniation is developed. Thus the device may be used pre-emptively to treat a defect.

One source of herniations is the migration of the nucleus pulposus material through the annulus, first causing fissures and ultimately weakening the disc. The device of the present invention may allow a substantially water-tight seal (or near to it) to be formed so as to prevent further migration of the nucleus pulposus. Furthermore, nucleus pulposus may cause sensitization of the nerves that grow into the annulus. Thus a water-tight seal is of further utility with specific application to annulus repair. Another potential advantage is that the device in accordance with an embodiment of the present invention allows a 360 degree suture to be created alongside the device, for closing/sealing a defect at both the inner and outer annular walls.

As outlined above, in some embodiments, the herniation is located within a region of an intervertebral disc and is treated by engaging and/or compressing the herniation from the outside, and distributing the compression force within the nucleus/annulus such that the load is shared by parts of the annulus that are more capable of handling the load. As mentioned above, in some embodiments, the device and methods disclosed may be used to treat a herniation along the posterior aspect of the annulus. Due to the proximity of the posterior aspect of the disc to sensitive neural structures, a herniation along the disc posterior may cause compression of the adjacent neural structures causing pain. Thus, the use of the device in accordance with an embodiment of the present invention, may be beneficial to reduce, stabilize or prevent the further growth of a herniation.

As outlined above, in the above applications, the inner portion is positioned internal to the tissue being treated with the outer portion position against the damaged portion external to the tissue. The coupling member allows the outer portion to be biased against the damaged portion while the inner member is biased against a healthy region of tissue away from the damaged portion and does not substantially apply a force against an inner surface of the tissue at the defect.

In some embodiments, the healthy region of tissue may sustain secondary injury or damage due to the force exerted by the inner member while the initial damaged region is treated. Thus, in some cases a secondary pathology may be created at the healthy region of tissue. Thus, a pathology or disease such as a herniation within the intervertebral disc may be shifted from the initial location to a secondary location within the disc. In other words the herniation may be transposed or relocated to another region of the disc. However, the impact of the herniation may be minimized as the secondary herniation may be located away from sensitive structures such as the spinal nerves branches. The secondary herniation may not compress, irritate, or sensitize structures that may be painful. In some embodiments, the inner portion may be have a larger surface area and may spread the force exerted by the inner portion over a larger area. Furthermore the inner member may have edges that are substantially atraumatic and may be for example curved or rounded. Thus, this may allow the force to be exerted over a greater inner surface area of the annulus and may allow the load (i.e. the force exerted by the nucleus pulposus at the defect creating a herniation) to be shared by regions of the annulus that support the inner portion. Thus an inner portion that has a relatively large surface area compared to the outer portion may help treat the defect such as a herniation without causing secondary affects such as a secondary herniation.

The patient population that may be treated using one or more embodiments disclosed herein includes patients having discs of varying heights/sizes and various disc pathologies including, but not limited to, disc height, nucleus degeneration, one or more herniations at various locations (example dorsal, ventral, lateral) and annular degeneration. In addition, some patients may have a plurality of herniations on a single disc or on multiple disc levels. Embodiments disclosed herein may be practiced in one or more of the cervical, thoracic and lumbar regions of the spine and may further be used to treat pathologies of various other anatomical structures such as, for example, joint capsules. In addition, embodiments of the present invention may be used to secure implantable devices.

Embodiments of methods disclosed herein may optionally be practiced in conjunction with one or more additional procedures, including but not limited to: vertebroplasty, fusion, discectomy, nucleotomy/nucleoplasty, radiofrequency or thermal denervation, nucleus replacement, interbody fusion and implantation of, for example, drug pumps, pacemakers or other electrical equipment.

In addition, embodiments of devices disclosed herein may optionally be compatible with one or more medical imaging modalities, including but not limited to magnetic resonance imaging, ultrasound, computed tomography, x-ray imaging and fluoroscopy.

Furthermore, embodiments of devices disclosed herein may optionally be usable via endoscopy, may be percutaneously deliverable (for example, as illustrated hereinabove) and/or may be used in conjunction with surgical forceps, rongeurs and needles.

The specific application described herein above, including specific features and advantages related thereto, relates to herniated discs. However, embodiments of a device and method of the present invention, in various configurations, can be used in other applications where tissues or other structures that have damage need reinforcement. The damage may be broad or focal.

For example, in accordance with various embodiments of the present invention, a device or method of the present invention may be utilized in various other applications such as meniscal repair, inguinal hernias, fractured vertebrae and blood vessel support. The inner portion, outer portion and the coupling member may be designed to have for example anchors and connecting members with relation to the type of tissue being supported. For instance, cloth/suture like materials may be used for devices used in blood vessel applications, whereas complete metal structures may be used for device used to treat vertebral body fractures.

In accordance with another specific embodiment of the present invention, the device may be used for meniscal repair. The damaged meniscus may delaminate or tear and the device allows for substantial reversal of the delamination, or for securing and/or containing the tear. In one example, the device can be used to substantially reverse the delamination and apply a radially outward force so that the meniscus exterior retains its natural shape more so than if the meniscus was compressed (in compression, the exterior aspect of the meniscus would be forced inwardly). In one embodiment, the outer portion is positioned within the joint space as it may be desirable to have no construct (such as the inner portion/coupling member) left within the joint space itself. Thus the inner portion may substantially not apply a force against the defect of the meniscus but rather applies a force to healthy tissue away from the defect, thus preventing the meniscus from being forced inwardly. Alternatively, in some embodiments the inner portion may be positioned within the joint space and the outer portion may be positioned outside. Thus, the device can be used in either direction, inside-out or outside-in (i.e. the outer portion or anchor would be on the inside or outside of the meniscus).

In still other embodiments, the device may comprise an inner and outer portion and a coupling member that comprise a suture and bone screw. For instance, for ligament repair, the outer portion, in some embodiments, is an anchor and the coupling member comprises a suture that is attached to the ligament itself. Finally, the inner portion or anchor may comprise an inner portion as described herein above, the inner portion being configured for positioning into bone. This may help avoid the use of bone screws and reduce the risk of screw loosening or expulsion.

Thus, The present disclosure describes embodiments for treating a defect in a region of tissue by applying a force at a surface of the tissue containing the defect to treat the defect while a counter-force is applied away from the region of tissue containing the defect, such that the counter-force is substantially not applied at the region of tissue containing the defect.

The embodiments described above are intended to be exemplary only. It is appreciated that certain features disclosed herein, which are, for clarity, described in the context of separate embodiments, may also be provided in combination in a single embodiment. Conversely, various features, which are, for brevity, described in the context of a single embodiment, may also be provided separately or in any suitable sub-combination.

Although various aspects disclosed herein have been described in conjunction with specific embodiments, it is evident that many alternatives, modifications and variations will be apparent to those skilled in the art. Accordingly, this disclosure is intended to embrace all such alternatives, modifications and variations that fall within the broad scope of the aspects described herein. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure.

We claim:

1. A method for treating a defect within a tissue comprising the steps of:
   (a) anchoring an inner portion of a device within a nucleus pulposus of an intervertebral disc at an inner wall of a disc annulus away from the defect by engaging a portion of the inner wall substantially without contacting an inner surface of a disc annulus at the defect;
   (b) positioning an outer portion of said device at an outer surface of the disc annulus of the intervertebral disc at the defect; and
   (c) applying a pulling force between said outer portion and said inner portion, such that said outer portion is forced against said outer surface at the defect while said inner portion does not substantially apply a force to said inner surface at the defect while applying a force to the inner wall of the disc annulus away from the defect.

2. The method of claim 1, wherein said inner portion is connected to said outer portion prior to, following or during step (a).

3. The method of claim 1, wherein the step of anchoring the inner portion comprises positioning said inner portion within said disc nucleus.

4. The method of claim 3, wherein the step of anchoring the inner portion further comprises deploying anchoring elements forming a part of, or being attached to, said inner portion.

5. The method of claim 1, wherein the inner portion is inserted into the intervertebral disc using an introducer device.

6. The method of claim 5, further comprising a step of retracting the introducer device.

7. The method of claim 6, wherein retracting the introducer device causes said inner portion to be anchored within the intervertebral disc, whereby at least a part of the inner portion engages an inner surface of the disc annulus.

8. The method of claim 6, wherein retracting the introducer device causes said inner portion to be anchored within the nucleus pulposus substantially without contacting an inner surface of the disc annulus.

9. The method of claim 6, wherein the step of retracting the introducer device allows the inner portion to move from a retracted position into an expanded position thereby anchoring the inner portion within the intervertebral disc.

10. The method of claim 1, wherein the step of anchoring the inner portion comprises applying force to the inner portion to expand the inner portion within the disc.

11. The method of claim 1, further comprising a step of connecting the outer portion to the inner portion via a coupling member.

12. The method of claim 1, wherein a coupling member is pre-attached to the inner portion and is inserted into the disc along with the inner portion.

13. The method of claim 12, further comprising a step of manipulating the coupling member.

14. The method of claim 13, wherein manipulating the coupling member comprises adjusting a length of the coupling member to reduce a distance between the inner portion and the outer portion.

15. The method of claim 11, wherein the coupling member applies a pulling force between said outer portion and said inner portion, such that said outer portion is forced against said outer surface at the defect while said inner portion does not substantially apply a force to said inner surface at the defect.

16. The method of claim 15, wherein the coupling member comprises a suture and a knot, and wherein the step of applying a pulling force comprises (i) pulling said inner portion radially outwards using the suture, and (ii) pushing said outer portion radially inwards using the knot and suture, to force said outer portion against said outer surface at said defect.

17. The method of claim 13, where the coupling member comprises a screw and wherein the step of manipulating the coupling member comprises actuating the screw.

18. The method of claim 1 wherein the defect comprises a herniation of the intervertebral disc.

19. The method of claim 1, wherein said defect comprises a tear within a region of the annulus.

20. The method of claim 1, wherein said defect comprises a delamination of the annulus.

21. The method of claim 1, wherein said defect comprises a substantially sealed discectomy hole.

22. The method of claim 21, wherein said defect comprises a substantially sealed discectomy hole that has been sealed using sutures.

23. The method of claim 1, wherein said defect comprises a fissure within a region of the annulus.

* * * * *